(12) United States Patent
Padwal et al.

(10) Patent No.: US 12,121,393 B2
(45) Date of Patent: Oct. 22, 2024

(54) AUTOMATED PROSTATE ANALYSIS SYSTEM

(71) Applicant: Verathon Inc., Bothell, WA (US)

(72) Inventors: Monali Padwal, Mercer Island, WA (US); Fuxing Yang, Bothell, WA (US); Joon Hwan Choi, Bothell, WA (US); Nasser Saber, Kirkland, WA (US); Nikolas Ivancevich, Seattle, WA (US)

(73) Assignee: Verathon Inc., Bothell, WA (US)

( * ) Notice: Subject to any disclaimer, the term of this patent is extended or adjusted under 35 U.S.C. 154(b) by 5 days.

(21) Appl. No.: 17/223,844

(22) Filed: Apr. 6, 2021

(65) Prior Publication Data

US 2021/0312652 A1    Oct. 7, 2021

Related U.S. Application Data

(60) Provisional application No. 63/006,468, filed on Apr. 7, 2020.

(51) Int. Cl.
*A61B 8/08* (2006.01)
*A61B 8/00* (2006.01)

(52) U.S. Cl.
CPC ............ *A61B 8/085* (2013.01); *A61B 8/4254* (2013.01); *A61B 8/4461* (2013.01); *A61B 8/46* (2013.01);
(Continued)

(58) Field of Classification Search
CPC ..... A61B 8/085; A61B 8/4245; A61B 8/4254; A61B 8/4455; A61B 8/4461;
(Continued)

(56) References Cited

U.S. PATENT DOCUMENTS

| 6,027,448 A | 2/2000 | Hossack et al. |
| 6,108,572 A | 8/2000 | Panda et al. |

(Continued)

FOREIGN PATENT DOCUMENTS

| JP | 2005-253751 A | 9/2005 |
| JP | 2007-98143 A | 4/2007 |

(Continued)

OTHER PUBLICATIONS

Shen et al. "Prostatic middle lobe hyperplasia correlates with bladder outflow obstruction: analysis of 131 cases." Zhonghua Nan Ke Xue. Jun. 2011;17(6):527-30. Chinese. PMID: 21735652. English Abstract only.

(Continued)

*Primary Examiner* — Katherine L Fernandez
*Assistant Examiner* — Brooke Lyn Klein
(74) *Attorney, Agent, or Firm* — Snyder, Clark, Lesch & Chung, LLP

(57) ABSTRACT

A system may include an ultrasound probe and a controller unit configured to aim the ultrasound probe to transabdominally image a patient's prostate and obtain a transabdominal image of the patient's prostate using the aimed ultrasound probe. The controller unit may be further configured to perform a segmentation process on the obtained transabdominal image of the patient's prostate using a trained machine learning model to identify a boundary of the prostate in the transabdominal image of the patient's prostate.

23 Claims, 17 Drawing Sheets

(52) U.S. Cl.
CPC .............. *A61B 8/467* (2013.01); *A61B 8/483* (2013.01); *A61B 8/485* (2013.01); *A61B 8/5223* (2013.01); *A61B 8/54* (2013.01); *A61B 8/4455* (2013.01); *A61B 8/4488* (2013.01); *A61B 8/465* (2013.01); *A61B 8/5292* (2013.01)

(58) Field of Classification Search
CPC ......... A61B 8/4488; A61B 8/46; A61B 8/465; A61B 8/467; A61B 8/483; A61B 8/485; A61B 8/488; A61B 8/5223; A61B 8/5292; A61B 8/54
See application file for complete search history.

(56) References Cited

U.S. PATENT DOCUMENTS

| | | | |
|---|---|---|---|
| 6,186,949 | B1 | 2/2001 | Hatfield et al. |
| 6,443,894 | B1 | 9/2002 | Sumanaweera et al. |
| 6,582,367 | B1 | 6/2003 | Robinson et al. |
| 8,273,026 | B2 | 9/2012 | Cerofolini |
| 8,323,201 | B2 | 12/2012 | Towfiq et al. |
| 2002/0040220 | A1* | 4/2002 | Zvuloni ............... A61B 8/0833 606/20 |
| 2006/0052699 | A1 | 3/2006 | Angelsen et al. |
| 2007/0167779 | A1 | 7/2007 | Kim et al. |
| 2009/0024030 | A1* | 1/2009 | Lachaine ............ A61B 8/14 600/437 |
| 2009/0182237 | A1* | 7/2009 | Angelsen ............ B06B 1/064 600/459 |
| 2010/0049053 | A1 | 2/2010 | Yamamoto et al. |
| 2011/0166564 | A1* | 7/2011 | Merrick ............ A61B 17/3205 606/115 |
| 2014/0057795 | A1* | 2/2014 | Xu ................... C12Q 1/6886 506/9 |
| 2018/0071554 | A1 | 3/2018 | Barthe et al. |
| 2018/0330518 | A1* | 11/2018 | Choi .................... G16H 30/20 |
| 2019/0099160 | A1* | 4/2019 | Choi .................... A61B 8/4466 |
| 2019/0148011 | A1* | 5/2019 | Rao .................... A61B 8/54 600/437 |
| 2020/0113542 | A1* | 4/2020 | Perrey .................. A61B 8/5207 |
| 2020/0345324 | A1* | 11/2020 | Matsumoto ............ A61B 8/54 |
| 2020/0402236 | A1* | 12/2020 | Courot ................ A61B 8/4416 |
| 2021/0192718 | A1* | 6/2021 | Brandl .................... G06T 7/11 |
| 2021/0219941 | A1* | 7/2021 | Tsutaoka ............ G01S 7/52046 |
| 2021/0353261 | A1* | 11/2021 | Ebata .................... G16H 50/30 |

FOREIGN PATENT DOCUMENTS

| | | | |
|---|---|---|---|
| JP | 2012-526623 A | 11/2012 | |
| JP | 5358636 B2 | 12/2013 | |
| WO | 2012/162413 A2 | 11/2012 | |
| WO | WO-2015119338 A1 * | 8/2015 | ............. A61B 8/085 |

OTHER PUBLICATIONS

Kim et al. "Correlations between the Various Methods of Estimating Prostate Volume: Transabdominal, Transrectal, and Three-Dimensional US." Korean J. Radiology 2008;9: pp. 134-139.

Yuen et al. "Effects of bladder vol. on transabdominal ultrasound measurements of intravesical prostatic protrusion and volume." May 2002, International Journal of Urology 9(4):225-9. Abstract only.

Kim et al.: Correlations between the Various Methods of Estimating Prostate vol. Transabdominal, Transrectal, and Three-Dimensional US. Korean J Radiol., Mar.-Apr. 2008; 9(2): 134-139.

Albayrak et al., Prostate Detection From Abdominal Ultrasound Images A Part Based Approach, 2015 IEEE International Conference on Image Processing (ICIP), 2015, 1955-1959.

Albayrak et al., Prostate Size Inference from Abdominal Ultrasound Images with Patch Based Prior Information, Springer International Publishing AG, Nov. 23, 2017 (Nov. 23, 2017), pp. 249-259.

PCT International Search Report and Written Opinion issued for the corresponding PCT application No. PCT/US2021/025996, mailed Jul. 12, 2021, 11 pages.

* cited by examiner

AUTOMATED PROSTATE ANALYSIS SYSTEM

PRIORITY INFORMATION

This patent application claims benefit of priority to U.S. Provisional Application No. 63/006,468, entitled "AUTOMATED PROSTATE ANALYSIS SYSTEM" and filed on Apr. 7, 2020, which is hereby incorporated herein by reference in its entirety.

BACKGROUND INFORMATION

An ultrasound probe may generate ultrasound signals using a transducer, such as, for example, a piezoelectric transducer or a capacitive transducer, which converts electrical signals into ultrasound energy and which converts received ultrasound echoes back into electrical signals. Ultrasound probes are typically used to identify a target organ or other structures in the body and/or determine features associated with the target organ/structure, such as the size of the organ/structure or the volume of fluid in the organ. For example, an ultrasound probe may be used to generate an ultrasound image of a region of interest and the ultrasound image may be processed or analyzed to identify a particular structure in the region of interest. Identifying particular structures in an ultrasound image may present various challenges.

DETAILED DESCRIPTION OF PREFERRED EMBODIMENTS

Figure 1A:
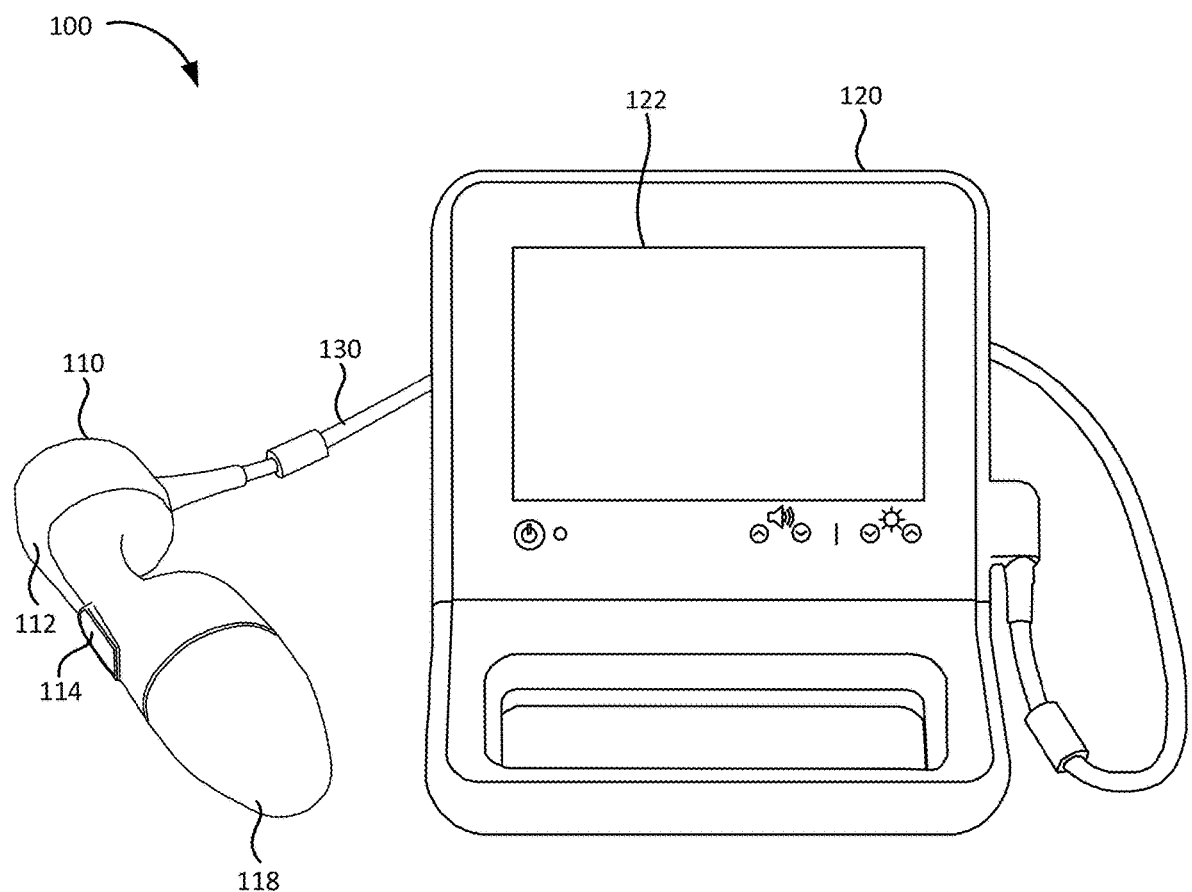
FIG. 1A is a diagram illustrating a first exemplary ultrasound system according to an implementation described herein.

The following detailed description refers to the accompanying drawings. The same reference numbers in different drawings identify the same or similar elements.

The measurement of the volume of the prostate gland is important for clinical decisions. For example, for male patients with Lower Urinary Tract Symptoms (LUTS) secondary to Benign Prostatic Hypertrophy (BPH), the prostate size may be important to predict response to medical therapy, risk for urinary retention, and/or need for future surgery. The Digital Rectal Exam (DRE) has been the mainstay of a standard physical exam for men above the age of 40 for evaluating the prostate for size, surface texture, firmness, and tenderness. However, the estimation of prostate size is qualitative and subjective, and different examiners may reach different conclusions. Furthermore, DRE does not provide an accurate method for evaluating the change in the size of the prostate over time. For example, studies show that an increase in prostate volume of only 30 milliliters (mL) is associated with a higher risk of developing acute urinary retention that may require surgical intervention and it may be very difficult to detect a change of such magnitude with DRE.

An imaging modality used for prostate assessment is Transrectal Ultrasound (TRUS). In TRUS, an ultrasound probe is inserted into a patient's rectum, which may be uncomfortable for the patient and inconvenient and/or inefficient for the examiner. Furthermore, to calculate the volume of a patient's prostate from ultrasound images, the examiner may need to obtain ultrasound images in multiple planes, measure the size of the prostate in each image, and use an ellipsoid calculation (e.g., height×length×width×$\pi$/6, etc.) to determine the volume of the prostate. Such manual calculations may be cumbersome and inefficient, and may result in an inaccurate determination of the volume of the prostate. For example, ellipsoid calculations assume that the prostate shape is a perfect ellipsoid, which may not be an accurate assumption.

Imaging with other modalities, such as Magnetic Resonant Imaging (MRI) or Computed Tomography (CT), may generate sectional slices of the prostate that may be used for volumetric contouring to generate a more accurate volume measurement of the prostate. However, these modalities are more expensive, time-consuming, and inconvenient to the patient in comparison to ultrasound. Furthermore, CT scans expose the patient to ionizing radiation.

Implementations described herein relate to an automated prostate analysis system that uses transabdominal ultrasound to capture images of the patient's prostate and that automatically calculates the size, volume, and/or shape of the patient's prostate based on the captured ultrasound images. Transabdominal ultrasound imaging may be more comfortable for the patient and easier to perform for the examiner in comparison to TRUS. Furthermore, automatic calculation of the size and volume of the patient's prostate from the captured transabdominal ultrasound images may be more efficient and more accurate than a manual calculation and/or a calculation based on an ellipsoid formula.

Thus, as described herein, a system includes a controller unit that includes a user interface and is in communication with an ultrasound probe for capturing ultrasound images. The controller unit may be configured to obtain an ultrasound image of the patient's lower abdominal area, identify an anatomical landmark in the obtained ultrasound image, and aim the ultrasound probe to transabdominally image the patient's prostate using the identified anatomical landmark as a reference point. Aiming the ultrasound probe may include redirecting the energy of the ultrasound probe in the direction of the patient's prostate. The controller unit may determine an aiming zone or area for the ultrasound probe using the identified anatomical landmark, which may include an identified back wall of the bladder, side wall of the bladder (and/or any other wall of the bladder), the pubic bone, a wall of the rectum, the prostate itself, and/or any other type of identified anatomical landmark in the obtained ultrasound image. Identifying the anatomical landmark may include performing a segmentation process on the obtained ultrasound image using a machine learning model trained to identify one or more different types of anatomical landmarks. In some implementations, aiming the ultrasound probe may include obtaining information from at least one of a position sensor or a pressure sensor located in the ultrasound probe.

In some implementations, the patient's bladder area may be imaged first, the obtained image of the bladder area may be used to aim the ultrasound probe, and the aimed ultrasound probe may be used to image the patient's prostate area. In other implementations, the patient's bladder area and prostate area may be imaged simultaneously, the obtained image of the combined bladder and prostate area may be used to aim the ultrasound probe, and the aimed ultrasound probe may be used to obtain a higher quality image, a more detailed image, and/or a different type of image of the patient's prostate area. In yet other implementations, the patient's prostate area may be imaged directly, the obtained image of the patient's prostate area may be used to aim the ultrasound probe, and the aimed ultrasound probe may be used to obtain a higher quality image, a more detailed image, and/or a different type of image of the patient's prostate area. In yet other implementations, the ultrasound probe may be aimed at the patient's prostate area without acquiring an ultrasound image to aid in aiming the ultrasound probe.

The controller unit may be further configured to obtain one or more transabdominal images of the patient's prostate using the aimed ultrasound probe and perform a segmentation process on the obtained transabdominal images of the patient's prostate using a trained machine learning model to identify a boundary of the prostate in the transabdominal images of the patient's prostate. The identified boundary of the prostate may be used to determine a size, volume, and/or shape of the patient's prostate. The determined size, volume, and/or shape of the patient's prostate may then be used to generate an analysis and/or recommendation (e.g., a recommendation for a medical intervention, etc.) based on the determined size, volume, and/or shape of the patient's prostate. Furthermore, the determined size, volume, and/or shape of the patient's prostate may be used to generate a risk prediction based on the determined size, volume, and/or shape of the patient's prostate. Additionally, the determined size, volume, and/or shape of the patient's prostate may be used to predict a change in the size of the patient's prostate in the future (e.g., over an upcoming number of years, etc.), to predict an outcome of a medical prostate reduction treatment, and/or to predict other aspects relating to the patient's prostate.

The analysis and/or recommendation may be based on the determined size, volume, and/or shape, or may be based on the determined size, volume, and/or shape combined with a clinically derived value. As an example, the recommendation may be based on a ratio of a Prostate-Specific Antigen (PSA) value, determined for the patient via a blood test, and the determined volume of the patient's prostate. As another example, a PSA/volume value may be weighted by the patient's age to generate a recommendation. As yet another example, a recommendation may be based on a calculated intravesical prostatic protrusion (IPP) value. An IPP value may measure how much a patient's prostate protrudes into the patient's bladder. A high IPP value may indicate difficulty in voiding urine, for example.

In some implementations, the risk prediction and/or clinical recommendation may be generated using a machine learning model trained to output a quantitative clinical grading value for the patient's prostate based on the determined size, volume, and/or shape. Furthermore, the size, volume, and/or shape of the patient's prostate may be compared to a previously determined size, volume, and/or shape obtained during a previous visit to determine a change in the size, volume, and/or shape of the patient's prostate. The determined change may be used to generate the risk prediction and/or clinical recommendation. Additionally, the same machine learning model, or a different machine learning model, may be used to determine whether the patient's prostate includes a lesion or an area of concern. The machine learning model may generate a likelihood that the patient's prostate includes a lesion or an area of concern and/or may perform segmentation to generate a boundary around an identified lesion or area of concern.

Moreover, the determined size, volume, and/or shape of the patient's prostate may be used to generate a recommendation to improve measurement of the determined size, volume, and/or shape of the patient's prostate. The recommendation may include at least one of a recommendation to adjust a position or angle of the ultrasound probe, a recommendation to the patient to drink water or another fluid, or a recommendation to address a detected artefact or interference in an ultrasound image, to obtain a better image of the prostate.

In some implementations, the ultrasound system may include a dual focus ultrasound transducer. The dual focus ultrasound transducer may include an outer element driven at a first frequency and an inner element driven at a second frequency that is higher than the first frequency. For example, the second frequency may correspond to a harmonic of the first frequency. The use of multiple frequencies may result in an extended depth of field, which results in better focus when imaging structures deeper in a patient's body, such as transabdominal imaging of the patient's prostate. Thus, obtaining the transabdominal images of the patient's prostate using the aimed ultrasound probe may include driving the dual focus ultrasound transducer in the ultrasound probe. Driving the dual focus ultrasound transducer may include generating an ultrasound signal that includes a fundamental frequency and at least one harmonic of the fundamental frequency.

In some implementations, obtaining the transabdominal images of the patient's prostate using the aimed ultrasound probe may include obtaining a set of three-dimensional (3D) ultrasound scan images of the patient's prostate. Furthermore, determining the size, volume, and/or shape of the prostate may include identifying a 3D boundary surface of the patient's prostate in the obtained 3D ultrasound scan images using a trained machine learning model.

Additionally, obtaining the transabdominal images of the patient's prostate may include obtaining one or more different types of ultrasound images, such as, for example, B-mode images (e.g., fundamental, harmonic and/or compounded, etc.), probability mode (P-mode) images, Doppler mode ultrasound images (e.g., Power Doppler, Continuous Wave Doppler, Pulsed Wave Doppler, etc.), motion mode (M-mode) ultrasound images, elastography ultrasound images, and/or any other type of imaging modality that uses ultrasound. A P-mode ultrasound image may correspond to an ultrasound image (e.g., a B-mode ultrasound image, etc.) in which each particular pixel is mapped to a probability indicating whether that particular pixel is within or part of a target organ/structure.

A machine learning model, as described herein, may include a computer program trained using a training set of images, and/or other types of input, to identify a particular feature in an image, to classify the image, or an identified feature in the image, into a particular class from a set of classes, and/or to output a numerical and/or categorical value for a particular parameter. In some implementations, a machine learning model may include a deep learning artificial neural network (DNN), such as a convolutional neural network (CNN). A CNN may be trained to develop multiple convolution matrices, also known as kernels, to identify features in ultrasound images, and/or optical images, including, for example, intensity transitions, shapes, texture information, etc., to identify a particular tissue structure and/or pathology in an image. The CNN, and/or another type of machine learning model, may be trained to perform classification, segmentation, and/or to output one or more values (e.g., a volume value, a size value, a numerical and/or categorical value representing a value on a clinical grading scale, etc.).

A CNN may include multiple layers of nodes, including an input layer, one or more convolution layers, one or more output computing layers, one or more pooling layers, and an output layer. A convolution layer may perform a convolution operation on the output of a set of nodes in the input layer associated with pixels within an area defined by the receptive field of the convolution layer. A pooling layer reduces a set of outputs from adjacent nodes in a convolution layer to reduce the dimensionality of a feature map generated by the convolutional layer. An output computing layer may generate an output for each node in a pooling layer based on an output function, such as, for example, a rectifier activation function. The output layer may include a fully connected layer that generates an output that identifies a feature of interest, that classifies an input into a particular class from a set of classes, and/or that outputs a numerical and/or categorical value for a parameter of interest.

A CNN may be trained using supervised learning, in which a set of images that has been labeled to identify a feature of interest, classified in a particular class from a set of classes, and/or to output a numerical and/or categorical value for a parameter of interest. For example, to train a CNN to perform segmentation to identify an implant capsule, a set of ultrasound images in which the implant capsule has been labeled may be used to train the CNN.

In other implementations, a different type of machine learning model may be used, such as, for example, a linear classifier, a naive Bayesian classifier, a kernel density estimation classifier, a decision tree classifier, a support vector machine classifier, a maximum entropy classifier, and/or another type of classifier. Furthermore, in other implementations, a machine learning model may be trained using unsupervised learning, in which input images have not been labeled with a predetermined classification. Moreover, in some implementations, the ultrasound system may include a "manual caliper" option to manually adjust the segmentation output of a machine learning model. For example, a user may be able to adjust the boundary of a prostate identified by a machine learning model, using a graphical user interface (GUI), keypad or keyboard inputs, etc. Additionally, the manual caliper option may enable a user to perform a manual segmentation without machine learning by defining a boundary of an organ, tissue, or area using the GUI or keypad/keyboard input. As an example, the user may draw the boundary or define a set of points that may be used to calculate the boundary. A user may select to use the manual caliper option to define the boundary when, for example, the machine learning model is determined by the user to be performing unsatisfactorily to determine the boundary. In some implementations, the user may manually select a set of seed points and the machine learning model may use the selected set of seed points together with the ultrasound image data to determine the boundary.

Although implementations described herein refer to scanning a prostate, in other implementations, other body areas, organs, joints, and/or vessels may be scanned. For example, implementations described herein may be used to assess the size, volume, and/or shape of an organ, tissue, or structure in another part of a patient's body that may be imaged using transabdominal ultrasound, such as, for example, the bladder, the kidneys, the colon, the small intestine, the pancreas, the ovaries, the uterus, and/or another organ, tissue, or structure. For example, an ultrasound system may include a bladder mode to scan and assess the size, volume, and/or shape of a patient's bladder, and a prostate mode to scan and assess the size, volume, and/or shape of the patient's prostate, and/or other modes to scan other body parts.

FIG. 1A is a diagram illustrating an exemplary ultrasound system 100 according to an implementation described herein. As shown in FIG. 1A, ultrasound system 100 may include an ultrasound probe 110, a controller unit 120, and a cable 130.

Ultrasound probe 110 may house one or more ultrasound transducers configured to generate ultrasound energy at a particular frequency and/or pulse repetition rate and to receive reflected ultrasound energy (e.g., ultrasound echoes) and convert the reflected ultrasound energy into electrical signals. For example, in some implementations, ultrasound probe 110 may be configured to transmit ultrasound signals with the center frequency in a range that extends from approximately two megahertz (MHz) to approximately 10 MHz or more. In other implementations, ultrasound probe 110 may be configured to transmit ultrasound signals in a different range. Furthermore, ultrasound probe 110 may house one or more motors for controlling the movement of the ultrasound transducer.

Ultrasound probe 110 may include a handle 112, a trigger 114, and a dome 118 (also referred to as a "nose"). A user (e.g., a medical practitioner, etc.) may hold ultrasound probe 110 via handle 112 and press trigger 114 to activate one or more ultrasound transceivers and transducers located in dome 118 to transmit ultrasound signals toward a patient's region of interest (e.g., a particular body organ, a body joint, a blood vessel, etc.). For example, probe 110 may be positioned on a pelvic area of a patient and over the patient's bladder and/or prostate.

Handle 112 enables a user to move probe 110 relative to a patient's region of interest. Activation of trigger 114 initiates an ultrasound scan of a selected anatomical portion while dome 118 is in contact with a surface portion of a patient's body when the patient's region of interest is scanned. Dome 118 may enclose one or more ultrasound transducers and may be formed from a material that provides an appropriate acoustical impedance match to the anatomical portion and/or permits ultrasound energy to be properly focused as it is projected into the anatomical portion. Dome 118 may also include transceiver circuitry that includes a transmitter and a receiver to transmit and receive ultrasound signals. Probe 110 may communicate with controller unit 120 via a wired connection, such as via cable 130. In other implementations, probe 110 may communicate with controller unit 120 via a wireless connection (e.g., Bluetooth, WiFi, etc.). In some implementations, probe 110 may not include dome 118.

Controller unit 120 may house and include one or more processors or processing logic configured to process reflected ultrasound energy that is received by probe 110 to produce an image of the scanned anatomical region. Furthermore, controller unit 120 may include display 122 to enable a user to view images from an ultrasound scan, and/or to enable operational interaction with respect to the user during operation of probe 110. For example, display 122 may include an output display/screen, such as a liquid crystal display (LCD), light emitting diode (LED) based display, touchscreen, and/or another type of display that provides text and/or image data to a user.

For example, display 122 may provide instructions to an operator for positioning probe 110 relative to a selected anatomical portion of a patient. Alternatively, ultrasound probe 110 may include a small display (e.g., in handle 112) that provides instructions for positioning ultrasound probe 110. Display 122 may also display two-dimensional or three-dimensional images of the selected anatomical region. In some implementations, display 122 may include a GUI that allows the user to select various features associated with an ultrasound scan. For example, display 122 may include selection items (e.g., buttons, dropdown menu items, checkboxes, etc.) to select particular transmission frequencies, to perform a particular action upon a captured ultrasound image (e.g., organ detection, fluid detection, tissue boundary detection, volume measurement, etc.), and/or other types of selections available to the user.

Additionally, display 122 may include selection items to select particular types of ultrasound images to be obtained, such as B-mode images (e.g., fundamental, harmonic and/or compounded, etc.), P-mode images, Doppler ultrasound images, M-mode images, elastography, and/or other types of ultrasound images. Moreover, display 122 may include selection items to select an aiming mode for probe 110 and/or to initiate a three-dimensional (3D) scan after probe 110 has been successfully positioned with respect to the patient's region of interest.

Figure 1B:
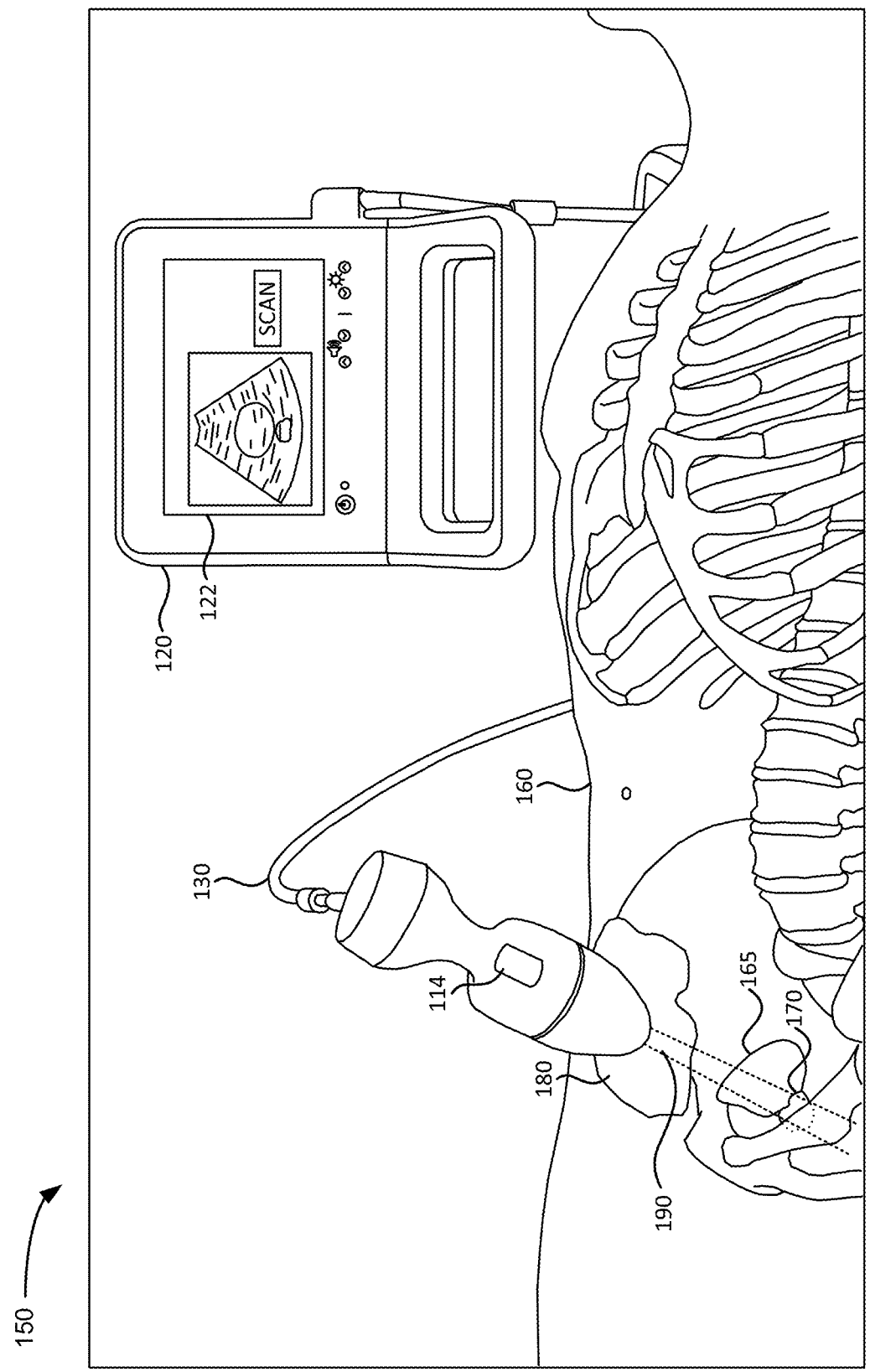
FIG. 1B is a diagram illustrating an exemplary environment for the ultrasound system of FIG. 1A according to an implementation described herein.

FIG. 1B is a diagram illustrating an exemplary environment 150 for ultrasound system 100 according to an implementation described herein. Environment 150 illustrates the operation of ultrasound system 100 with respect to a patient 160. As shown in FIG. 1B, patient 160 may be positioned so that a patient's region of interest may be scanned. For example, assume the region of interest corresponds to the patient's bladder 165 and/or prostate 170. To scan prostate 170, ultrasound probe 110 may be positioned against a surface portion of patient 160 that is proximate to the anatomical portion to be scanned. The user may apply acoustic gel 180 (or gel pads) to the skin of patient 160 over the area of prostate 170 to provide an acoustical impedance match when dome 118 is placed against the skin.

The user may select an aiming mode via controller unit 120 (e.g., by selecting an aiming mode button, menu item, etc., on display 122, by speaking a voice command, etc.). Alternatively, an aiming mode may be selected automatically when controller unit 120 detects motion of ultrasound probe 110 or ultrasound probe 110 contacts acoustic gel 180 or the skin of patient 160 (e.g., via an accelerometer and/or gyroscope inside ultrasound probe 110). Ultrasound probe 110 may transmit ultrasound signals 190 through bladder 165 and prostate 170 and may receive reflected ultrasound signals. The reflected ultrasound signals may be processed into images that are displayed on display 122.

Although FIGS. 1A and 1B show exemplary components of ultrasound system 100, in other implementations, ultrasound system 100 may include fewer components, different components, additional components, or differently arranged components than depicted in FIGS. 1A and 1B. Additionally or alternatively, one or more components of ultrasound system 100 may perform one or more tasks described as being performed by one or more other components of ultrasound system 100.

For example, in other embodiments, ultrasound probe 110 may correspond to a self-contained device that includes a microprocessor housed within ultrasound probe 110, configured to operably control the one or more ultrasound transducers, and to process the reflected ultrasound energy to generate ultrasound images. Accordingly, a display on ultrasound probe 110 may be used to display the generated images and/or to view other information associated with the operation of ultrasound probe 110. In yet other implementations, ultrasound probe 110 may be coupled to a general-purpose computer, such as a laptop, tablet, smart phone, and/or a desktop computer (via a wired or wireless connection) that includes software that at least partially controls the operation of ultrasound probe 110 and/or that includes software to process information received from ultrasound probe 110 to generate ultrasound images.

Figure 2A:
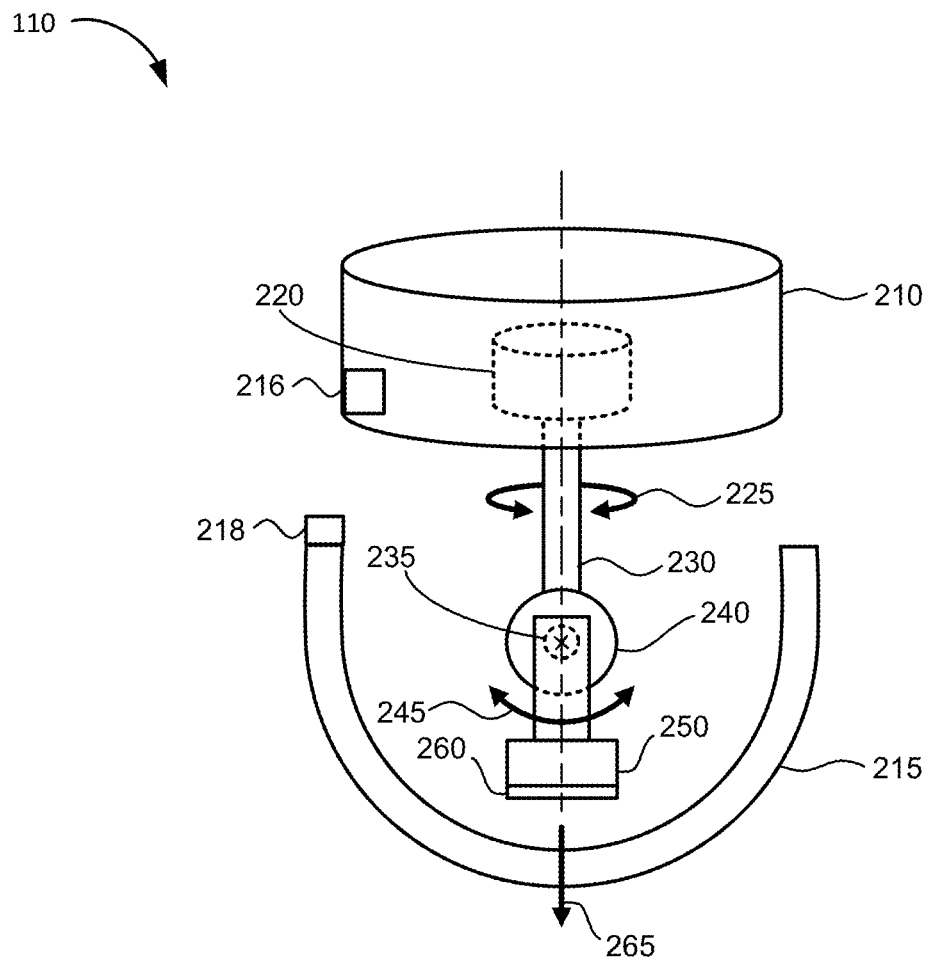
FIGS. 2A-2D are diagrams of exemplary ultrasound probes, respectively, according to implementations described herein.

FIG. 2A is a diagram of a first exemplary implementation of ultrasound probe 110 according to an implementation described herein. As shown in FIG. 2A, ultrasound probe 110 may include a single transducer element coupled to two rotational motors. In this implementation, ultrasound probe 110 may include a base 210 connected to a dome 215, a theta motor 220, a spindle 230, a phi motor 240, and a transducer bucket 250 with a transducer 260. Theta motor 220, phi motor 240, and/or transducer 260 may include wired or wireless electrical connections that electrically connect theta motor 220, phi motor 240, and/or transducer 260 to controller unit 120.

Dome 215 may enclose transducer bucket 250 and may be formed from a material that provides an appropriate acoustical impedance match to the anatomical portion and/or permits ultrasound energy to be properly focused as it is projected into the anatomical portion. Base 210 may house theta motor 220 and provide structural support to ultrasound probe 110. Base 210 may connect to dome 215 and may form a seal with dome 215 to protect the components of ultrasound probe 110 from the external environment. Theta motor 220 may rotate spindle 230 with respect to base 210 in a longitudinal direction with respect to transducer 260, by rotating around a vertical axis referred to herein as a theta (θ) rotational plane 225. Spindle 230 may terminate in a shaft 235 and phi motor 240 may be mounted onto shaft 235. Phi motor 240 may rotate around an axis orthogonal to the theta rotational plane 225 around a horizontal axis referred to herein as a phi (ϕ) rotational plane 245. Transducer bucket 250 may be mounted to phi motor 240 and may move with phi motor 240.

Transducer 260 may be mounted to transducer bucket 250. Transducer 260 may include a piezoelectric transducer, a capacitive transducer, a micro-electromechanical system (MEMS) transducer, and/or another type of ultrasound transducer. Transducer 260, along with transceiver circuitry associated with transducer 260, may convert electrical signals to ultrasound signals at a particular ultrasound frequency or range of ultrasound frequencies, may receive reflected ultrasound signals (e.g., echoes, etc.), and may convert the received ultrasound signals to electrical signals. Transducer 260 may transmit and receive ultrasound signals in a signal direction 265 that is substantially perpendicular to the surface of transducer 260.

Signal direction 265 may be controlled by the movement of phi motor 240 and the orientation of phi motor may be controlled by theta motor 220. For example, phi motor 240 may rotate back and forth across an angle that is less than 180 degrees to generate ultrasound image data for a particular plane and theta motor 220 may rotate to particular positions to obtain ultrasound image data for different planes.

In a 3D scan mode, theta motor 220 may cycle through a set of planes one or more times to obtain a full 3D scan of an area of interest. In each particular plane of the set of planes, phi motor 240 may rotate to obtain ultrasound image data for the particular plane. The movement of theta motor 220 and phi motor 240 may be interlaced in the 3D scan motor. For example, the movement of phi motor 240 in a first direction may be followed by a movement of theta motor 220 from a first plane to a second plane, followed by the movement of phi motor 240 in a second direction opposite to the first direction, followed by movement of theta motor 220 from the second plane to a third plane, etc. Such interlaced movement may enable ultrasound probe 110 to obtain smooth continuous volume scanning as well as improving the rate at which the scan data is obtained.

Additionally, as shown in FIG. 2A, ultrasound probe 110 may include a position sensor 216 and a pressure sensor 218. Position sensor 216 may include an accelerometer, gyroscope, and/or magnetometer configured to measure changes in the position of ultrasound probe 110. Pressure sensor 218 may include a piezoelectric pressure sensor, a capacitive pressure sensor, an inductive pressure sensor, a strain gauge pressure sensor, a thermal pressure sensor, a MEMS sensor, and/or another type of sensor to sense pressure applied against ultrasound probe 110. Position sensor 216 and/or pressure sensor 218 may be used to help an operator accurately position ultrasound probe 110 during aiming and/or scanning by providing feedback and/or instructions to the operator. While position sensor 216 and pressure sensor 218 are shown in particular locations on ultrasound probe 110 in FIG. 2A, in other implementations, position sensor 216 and/or pressure sensor 218 may located anywhere on ultrasound probe 110.

Figure 2B:
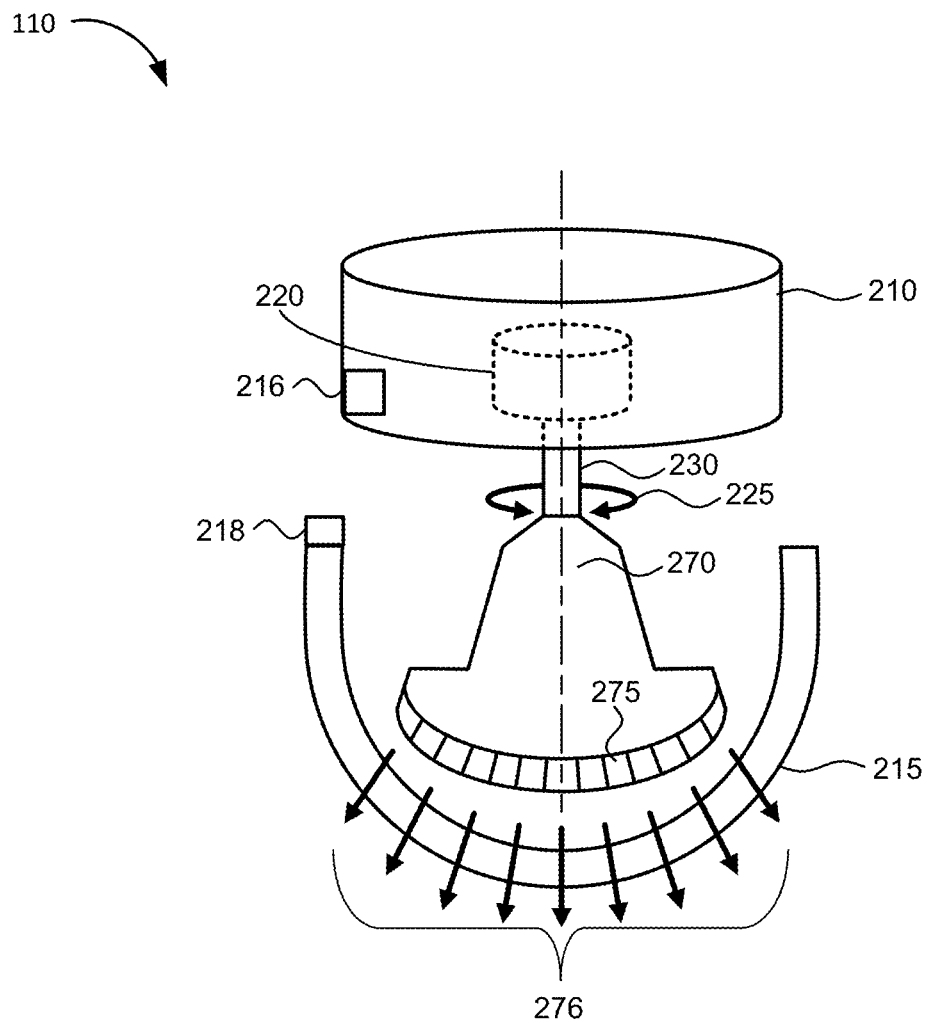

FIG. 2B is a diagram of a second exemplary implementation of ultrasound probe 110 according to an implementation described herein. As shown in FIG. 2B, ultrasound probe 110 may include a one-dimensional (1D) array of transducer elements coupled to a rotation motor. In this implementation, ultrasound probe 110 may include a base 210 connected to dome 215, a theta motor 220, a spindle 230, and a transducer bucket 270 with a 1D transducer array 275. Theta motor 220 and/or 1D transducer array 275 may include wired or wireless electrical connections that electrically connect theta motor 220 and/or 1D transducer array 275 to controller unit 120.

Base 210 may house theta motor 220 and provide structural support to ultrasound probe 110. Base 210 may connect to dome 215 and may form a seal with dome 215 to protect the components of ultrasound probe 110 from the external environment. Theta motor 220 may rotate spindle 230 with respect to base 210 in longitudinal direction with respect to 1D transducer array 275 by rotating around theta rotational plane 225. Spindle 230 may terminate in transducer bucket 270. 1D transducer array 275 may be mounted to transducer bucket 270. 1D transducer array 275 may include a curved 1D array of piezoelectric transducers, capacitive transducers, MEMS transducers, and/or other types of ultrasound transducers. 1D transducer array 275 may convert electrical signals to ultrasound signals at a particular ultrasound frequency or range of ultrasound frequencies, may receive reflected ultrasound signals (e.g., echoes, etc.), and may convert the received ultrasound signals to electrical signals. Each element, or a group of elements, of 1D transducer array 275 may transmit and receive ultrasound signals in a particular direction of a set of directions, illustrated as item 276 in FIG. 2B. In other implementations, 1D transducer array 275 may be controlled to electronically tilt an ultrasound beam in a particular direction. Thus, together, the elements of 1D transducer array 275 may generate ultrasound image data for a particular plane. In a 3D scan mode, theta motor 220 may cycle through a set of planes one or more times to obtain a full 3D scan of an area of interest. In each particular plane of the set of planes, 1D transducer array 275 may obtain ultrasound image data for the particular plane. In some implementations, ultrasound probe 110 may not include theta motor 220 and/or dome 215. For example, ultrasound probe 110 may correspond to a hand-held probe that is moved manually by a user to different positions. Additionally, as shown in FIG. 2B, ultrasound probe 110 may include position sensor 216 and pressure sensor 218.

Figure 2C:
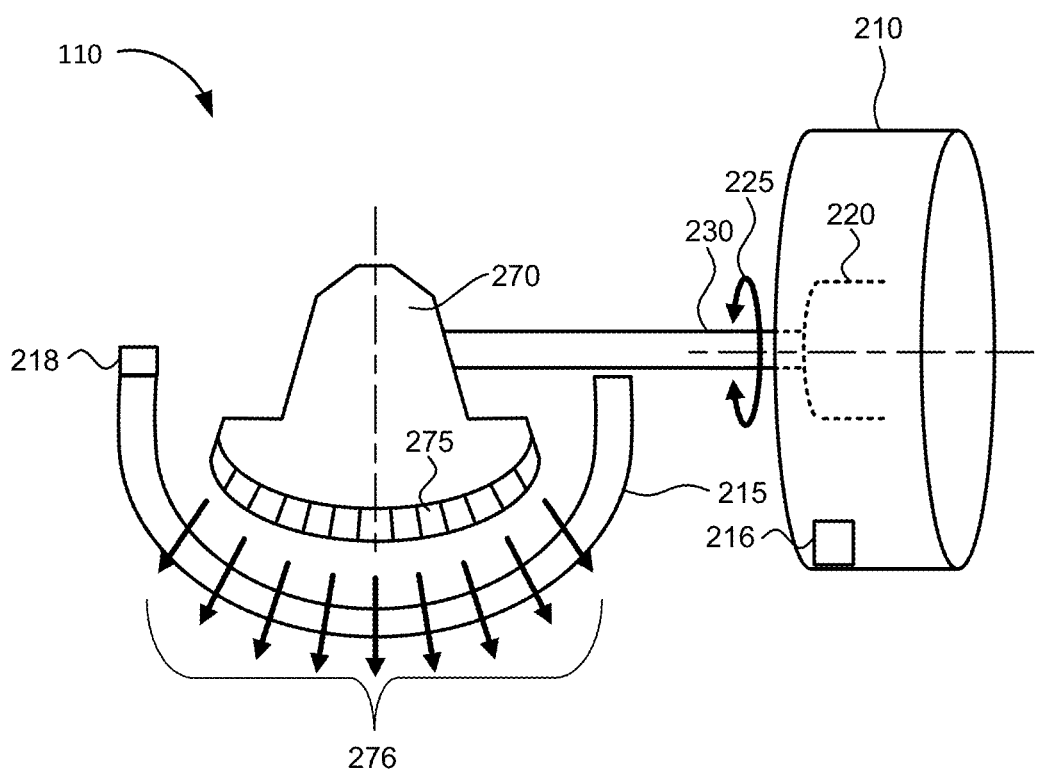

FIG. 2C is a diagram of a third exemplary ultrasound probe 110 according to an implementation described herein. While in second exemplary ultrasound probe 110 of FIG. 2B, 1D transducer array 275 rotates around spindle 230 in a longitudinal direction with respect to 1D transducer array 275, in third exemplary ultrasound probe 110 of FIG. 2C, 1D transducer array 275 rotates around spindle 230 in a transverse direction with respect to 1D transducer array 275, causing 1D transducer array 275 to move back and forth in a fan-like motion. As shown in FIG. 2C, ultrasound probe 110 may include 1D transducer array 275 mounted to transducer bucket 270 with base 210, theta motor 220, and spindle 230 mounted in a horizontal direction with respect to 1D transducer array 275 and positioned perpendicularly to the center of set of directions 276. Thus, theta motor 220 may rotate spindle 230 with respect to base 210 in a transverse direction with respect to 1D transducer array 275 by rotating around theta rotational plane 225, causing 1D transducer array 275 to move back and forth in a fan-like motion. Additionally, as shown in FIG. 2C, ultrasound probe 110 may include position sensor 216 and pressure sensor 218.

Figure 2D:
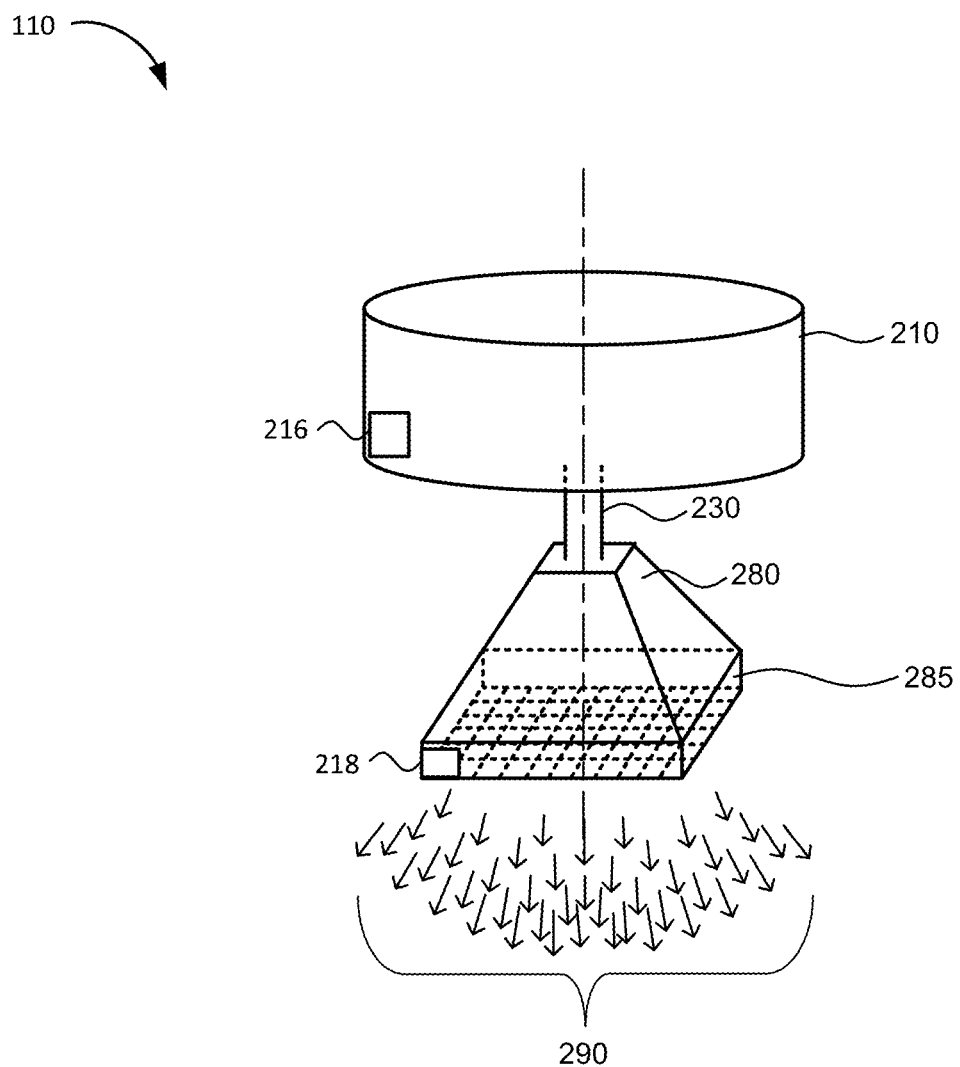

FIG. 2D is a diagram of a fourth exemplary ultrasound probe 110 according to an implementation described herein. As shown in FIG. 2D, ultrasound probe 110 may include a two-dimensional (2D) array of transducer elements. In this implementation, ultrasound probe 110 may include a base 210, a spindle 230, and a transducer bucket 280 with a 2D transducer array 285. 2D transducer array 285 may include wired or wireless electrical connections that electrically connects 2D transducer array 285 to controller unit 120.

Base 210 may provide structural support to ultrasound probe 110 and secure spindle 230. Spindle 230 may terminate in transducer bucket 280. 2D transducer array 285 may be mounted to transducer bucket 280. 2D transducer array 285 may include a 2D array of piezoelectric transducers, capacitive transducers, MEMS transducers, and/or other types of ultrasound transducers. 2D transducer array 285 may convert electrical signals to ultrasound signals at a particular ultrasound frequency or range of ultrasound frequencies, may receive reflected ultrasound signals (e.g., echoes, etc.), and may convert the received ultrasound signals to electrical signals. Each element of 2D transducer array 285 may transmit and receive ultrasound signals in a particular direction of a set of directions, illustrated as item 290 in FIG. 2D. Thus, together, the elements of 2D transducer array 285 may generate ultrasound image data for multiple planes to generate a 3D ultrasound scan. In other words, 2D transducer array 285 may be controlled to tilt an ultrasound beam electronically in a particular direction. In a 3D scan mode, 2D transducer array 285 may cycle through sets of 1D sets of transducer elements one or more times to obtain a full 3D scan of an area of interest. Alternatively, multiple sets of 1D sets of transducer elements, or even all of the transducer elements, of 2D transducer array 285 may be activated substantially simultaneously to obtain a full 3D scan of the area of interest. Additionally, as shown in FIG. 2D, ultrasound probe 110 may include position sensor 216 and pressure sensor 218.

Although FIGS. 2A, 2B, 2C, and 2D show exemplary components of ultrasound probe 110, in other implementations, ultrasound probe 110 may include fewer components, different components, additional components, or differently arranged components than depicted in FIGS. 2A, 2B, 2C, and 2D. Additionally or alternatively, one or more components of ultrasound probe 110 may perform one or more tasks described as being performed by one or more other components of ultrasound probe 110.

Figure 3A:
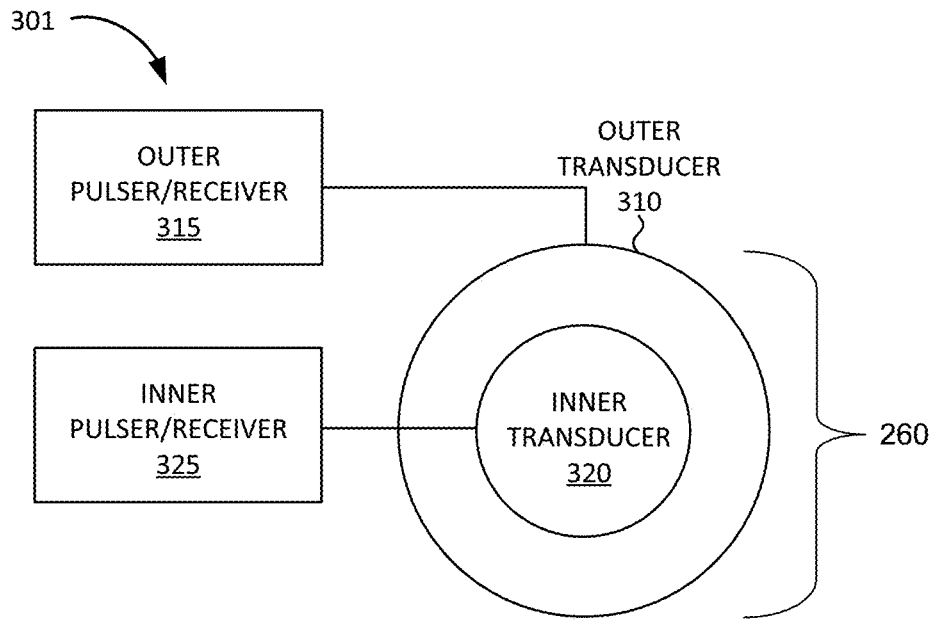
FIGS. 3A and 3B are diagrams of a first and second view of a dual element transducer, which may be included in a probe shown in FIGS. 2A-2D.
Figure 3B:
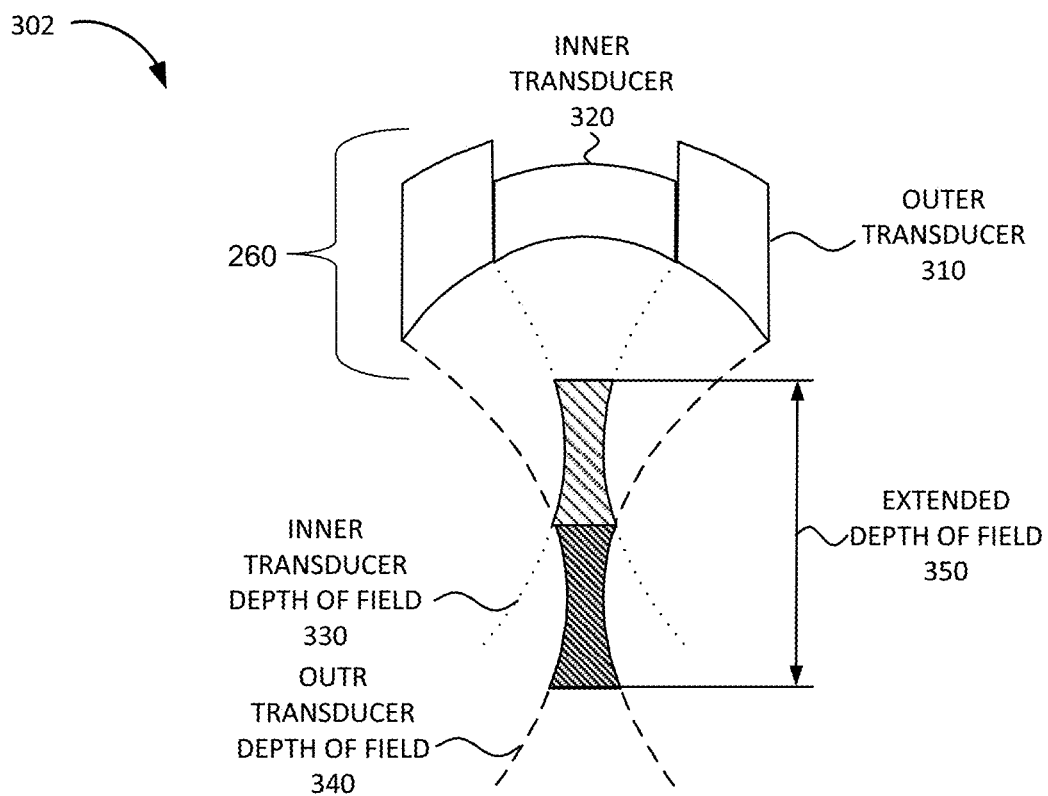

FIGS. 3A and 3B are diagrams of a first view 301 and a second view 302, respectively, of a dual element transducer 260 that may be included in any of the probes shown in FIG. 2A. As shown in first view 301 of FIG. 3A, corresponding to a plane perpendicular to transmitted and received ultrasound signals (e.g., perpendicular to signal directions 265, 276, or 290), transducer 260 may include an outer transducer element 310 and an inner transducer element 320. Outer transducer element 310 may be coupled to an outer transducer pulser/receiver 315 and inner transducer element 320 may be coupled to an inner transducer pulser/receiver 325. Outer transducer pulser/receiver 315 may drive outer transducer element 310 to pulse at a first frequency and inner transducer pulser/receiver 325 may drive inner transducer element 325 to pulse at a second frequency. As an example, the second frequency may be a harmonic of the first frequency (e.g., a first harmonic, a second harmonic, etc.). As another example, the transmission frequencies of outer transducer element 310 and an inner transducer element 320 may be offset by a particular difference. For example, outer transducer element 310 may transmit ultrasound signals at a frequency of $3+\Delta$ MHz and inner transducer element 310 may transmit ultrasound signals at a frequency of $3-\Delta$ MHz, where $\Delta$ is the selected frequency offset. Furthermore, outer transducer pulser/receiver 315 and inner transducer pulser/receiver 325 may detect and receive ultrasound signal echoes received by outer transducer element 310 and inner transducer element 320, respectively.

In some implementations, outer transducer element 310 may transmit ultrasound signals at a lower frequency and lower bandwidth and may be used for a spatially long acoustic radiation force pulse. Inner transducer element 320 may transmit ultrasound signals at a higher frequency and higher bandwidth, and may be used for the tracking of induced shear waves. As an example, outer transducer element 310 may transmit ultrasound pulses at a frequency of $f_0$ and inner transducer element 320 may receive an echo from the first harmonic with a resonance at a frequency of $2*f_0$.

In some implementations, the transducer frequencies may be optimized for differential harmonics. For example, outer transducer element 310 may transmit ultrasound pulses at a frequency of $f_0$, inner transducer element 320 may transmit ultrasound pulses at a frequency of $f_1$, outer transducer element 310 may measure returned echo signals at frequency $f_1-f_0$, and inner transducer element 320 may measure returned echo signals at frequency $2*f_0$.

Second view 302 of FIG. 3B illustrates a side view of dual element transducer 260 with respect to first view 301. As shown in FIG. 3B, in some implementations, outer transducer element 310 and inner transducer element 320 may form a concave parabolic surface in a plane perpendicular to the direction of transmitted and received signals. The concave parabolic surface, together with the difference in the transmitted frequencies, may result in an extended depth of field 350 based on a combination of an inner transducer depth of field 330 and an outer transducer depth of field 340. Thus, the design of dual element transducer 260 may be optimized to extend the depth of field of the transmitted ultrasound signals, while maintaining uniformity in the axial and lateral beam dimensions, based on the dimensions, shape, and relative geometric focus offset of outer transducer element 310 and inner transducer element 320, and based on the selected frequencies transmitted and measured by each of outer transducer element 310 and inner transducer element 320. For example, the depth of focus of dual element transducer 260 may be extended to at least 18 centimeters (cm).

Figure 4:
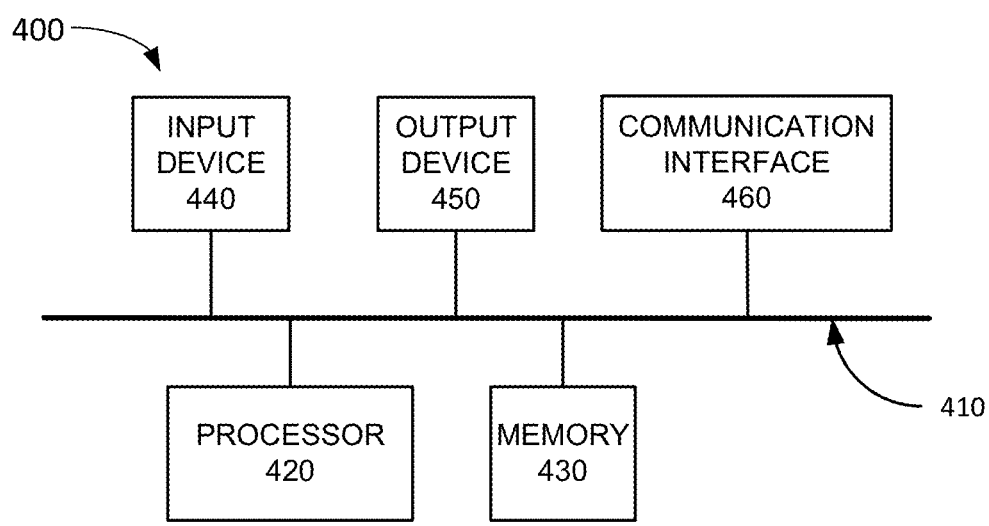
FIG. 4 is a diagram illustrating exemplary components of a device that is included in one or more components of the system of FIGS. 1A and 1B.

FIG. 4 is a diagram illustrating exemplary components of a device 400 according to an implementation described herein. Controller unit 120, display 122, and/or ultrasound probe 110 may each include one or more devices 400. As shown in FIG. 4, device 400 may include a bus 410, a processor 420, a memory 430, an input device 440, an output device 450, and a communication interface 460.

Bus 410 may include a path that permits communication among the components of device 400. Processor 420 may include any type of single-core processor, multi-core processor, microprocessor, latch-based processor, and/or processing logic (or families of processors, microprocessors, and/or processing logics) that interprets and executes instructions. In other embodiments, processor 420 may include an application-specific integrated circuit (ASIC), a field-programmable gate array (FPGA), and/or another type of integrated circuit or processing logic.

Memory 430 may include any type of dynamic storage device that may store information and/or instructions, for execution by processor 420, and/or any type of non-volatile storage device that may store information for use by processor 420. For example, memory 430 may include a random access memory (RAM) or another type of dynamic storage device, a read-only memory (ROM) device or another type of static storage device, a content addressable memory (CAM), a magnetic and/or optical recording memory device and its corresponding drive (e.g., a hard disk drive, optical drive, etc.), and/or a removable form of memory, such as a flash memory.

Input device 440 may allow an operator to input information into device 400. Input device 440 may include, for example, a keyboard, a mouse, a pen, a microphone, a remote control, an audio capture device, an image and/or video capture device, a touch-screen display, and/or another type of input device. In some embodiments, device 400 may be managed remotely and may not include input device 440. In other words, device 400 may be "headless" and may not include a keyboard, for example.

Output device 450 may output information to an operator of device 400. Output device 450 may include a display, a printer, a speaker, and/or another type of output device. For example, device 400 may include a display, which may include a liquid-crystal display (LCD) for displaying content to the customer. In some embodiments, device 400 may be managed remotely and may not include output device 450. In other words, device 400 may be "headless" and may not include a display, for example.

Communication interface 460 may include a transceiver that enables device 400 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. Communication interface 460 may include a transmitter that converts baseband signals to radio frequency (RF) signals and/or a receiver that converts RF signals to baseband signals. Communication interface 460 may be coupled to an antenna for transmitting and receiving RF signals.

Communication interface 460 may include a logical component that includes input and/or output ports, input and/or output systems, and/or other input and output components that facilitate the transmission of data to other devices. For example, communication interface 460 may include a network interface card (e.g., Ethernet card) for wired communications and/or a wireless network interface (e.g., a WiFi) card for wireless communications. Communication interface 460 may also include a universal serial bus (USB) port for communications over a cable, a Bluetooth™ wireless interface, a radio-frequency identification (RFID) interface, a near-field communications (NFC) wireless interface, and/or any other type of interface that converts data from one form to another form.

As will be described in detail below, device 400 may perform certain operations relating to capturing transabdominal ultrasound images of a patient's prostate, automated measurements of the size, volume, and/or shape of the patient's prostate, and/or recommendations based on the measurements. Device 400 may perform these operations in response to processor 420 executing software instructions contained in a computer-readable medium, such as memory 430. A computer-readable medium may be defined as a non-transitory memory device. A memory device may be implemented within a single physical memory device or spread across multiple physical memory devices. The software instructions may be read into memory 430 from another computer-readable medium or from another device. The software instructions contained in memory 430 may cause processor 420 to perform processes described herein. Alternatively, hardwired circuitry may be used in place of, or in combination with, software instructions to implement processes described herein. Thus, implementations described herein are not limited to any specific combination of hardware circuitry and software.

Although FIG. 4 shows exemplary components of device 400, in other implementations, device 400 may include fewer components, different components, additional components, or differently arranged components than depicted in FIG. 4. Additionally, or alternatively, one or more components of device 400 may perform one or more tasks described as being performed by one or more other components of device 400.

Figure 5:
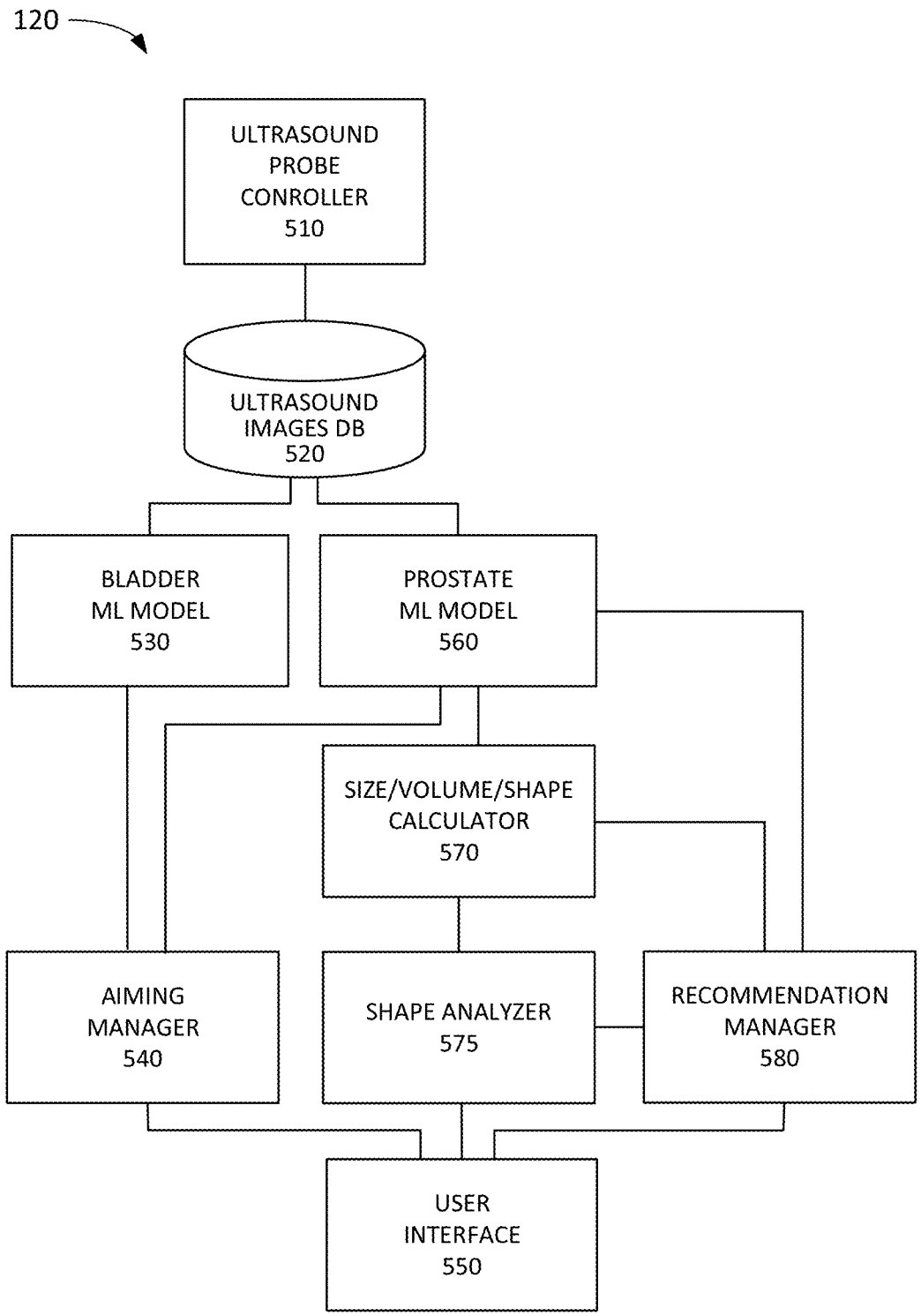
FIG. 5 is a diagram illustrating exemplary functional components of the system of FIGS. 1A and 1B.

FIG. 5 is a diagram illustrating exemplary functional components of controller unit 120. The functional components of controller unit 120 may be implemented, for example, via processor 420 executing instructions from memory 430. Alternatively, some or all of the functional components of controller unit 120 may be implemented via hard-wired circuitry. As shown in FIG. 5, controller unit 120 may include an ultrasound probe controller 510, an ultrasound images database (DB) 520, a bladder machine learning (ML) model 530, an aiming manager 540, a user interface 550, a prostate ML model 560, a size/volume/shape calculator 570, a shape analyzer 575, and a recommendation manager 580.

Ultrasound probe controller 510 may be configured to control ultrasound probe 110 and to collect ultrasound image data from ultrasound probe 110. For example, ultrasound probe controller 510 may perform a 3D scan of a patient's lower abdominal area by generating ultrasound images in particular planes by controlling one or more motors and/or particular transducers of ultrasound probe 110. For example, ultrasound probe controller 510 may control ultrasound probe 110 to perform a 3D scan that includes all radial, antiradial, sagittal, and transverse planes in the focus zone of ultrasound probe 110. Ultrasound probe controller 510 may control outer transducer pulser/receiver 315 and inner transducer pulser/receiver 325 to cause outer transducer 310 and inner transducer 320 to each transmit ultrasound signals at a particular frequency or frequency range and/or to receive ultrasound signals at a particular frequency or frequency range. Ultrasound probe controller 510 may obtain B-mode images (e.g., fundamental, harmonic and/or compounded, etc.), P-mode images, Doppler mode ultrasound images, M-mode ultrasound images, elastography ultrasound images, and/or any other type of ultrasound images. Ultrasound probe controller 510 may store obtained ultrasound images in ultrasound images DB 520.

Bladder ML model 530 may include a CNN model and/or another type of ML model trained to perform segmentation to identify the boundaries of a bladder in ultrasound images. For example, bladder ML model 530 may identify the back wall, side wall, and/or front wall of a bladder in a set of one or more ultrasound images. In some implementations, other types of ML models may be included that are trained to identify other types of anatomical landmarks.

Aiming manager 540 may determine an aiming zone for ultrasound probe 110 to image the patient's prostate, based on an anatomical landmark identified by bladder ML model 530. For example, aiming manager 540 may identify an area of particular dimensions (e.g., a particular length and width) and locate the identified area a particular distance from the identified anatomical landmark, such as the identified back wall of the bladder.

Aiming manager 540 may then aim ultrasound probe 110 to image the patient's prostate based on the determined aiming zone to ensure that the ultrasound signals from ultrasound probe 110 reach the intended target (e.g., the patient's prostate). For example, aiming manager 540 may send instructions to the operator, via user interface 550, to move and/or tilt ultrasound probe 110 in a particular direction to position ultrasound probe 110 to accurately image the patient's prostate. Additionally, or alternatively, aiming manager 540 may adjust the extended depth of field 350 of transducer 260 by selecting a first frequency, or frequency range, for outer transducer 310 and selecting a second frequency, or frequency range, for inner transducer 320 to enable the signals transmitted by ultrasound probe 110 to reach the required depth of field for imaging the prostate.

Aiming manager 540 may ensure the best possible coverage of the prostate. For example, if the prostate is located at off center at 15° in the theta direction (e.g., with respect to the movement of theta motor 220) and 12° in the phi direction (e.g., with respect to the movement of phi motor 240), the 3D ultrasound scan to determine the volume of the prostate may be performed with a shifted origin of 15° in the theta direction and 12° in the phi direction. Furthermore, aiming manager 540 may adjust the acoustic and acquisition parameters based on the estimated prostate location determined using the determined aiming zone. The adjusted parameters may include the focus position of ultrasound probe 110, the scanning aperture, the scan depth, the line density, the scan plane density, and the transmission frequencies.

User interface 550 may generate or include a user interface (e.g., a graphical user interface) that displays ultrasound images to a user via display 122, displays instructions and/or recommendations to the user, and that is configured to receive selections and/or commands from the user via a touchscreen associated with display 122, via one or more control keys located on controller unit 120, on ultrasound probe 110, via a microphone included in controller unit 120, and/or via another type of input method.

For example, a user may select to image a particular organ, tissue, or structure (e.g., prostate), a particular type of ultrasound image to obtain, to perform a 3D ultrasound scan, select to perform an elastography ultrasound scan, select to retrieve a patient record that includes previously obtained ultrasound images, select to perform a comparison of baseline and follow-up ultrasound images, select to use a machine learning model to perform segmentation and analysis of an ultrasound image, select to identify pathologies in an ultrasound image using a machine learning model, and/or select to perform another type of function for which controller unit 120 has been configured.

Prostate ML model 560 may include a CNN model and/or another type of ML model trained to perform segmentation to identify the boundaries of a prostate in ultrasound images. In some implementations, prostate ML model 560 may be trained to perform segmentation to identify the boundaries of a prostate in a two-dimensional (2D) ultrasound image. Additionally, or alternatively, prostate ML model 560 may be trained to perform segmentation to identify a 3D surface of a prostate in a set of ultrasound images obtained during a 3D ultrasound scan. As an example, prostate ML model 560 may perform segmentation on individual 2D images from the set of 3D scan images to identify the boundary of the prostate in each image, and may then stitch together or otherwise combine the boundaries from the individual ultrasound images to generate a 3D surface of the prostate.

Furthermore, in some implementations, prostate ML model 560, or another ML model, may be trained to classify a segmented prostate into a particular size category. Moreover, in some implementations, prostate ML model 560, or another ML model, may be trained to compare a base line ultrasound image of a patient's prostate with a follow-up ultrasound image of the patient's prostate to determine how much the size, shape, and/or volume of the patient's prostate has changed over time. Additionally, in some implementations, prostate ML model 560, or another ML model, may be trained to identify a particular pathology in a patient's prostate, such as a lesion or an area of concern.

In some implementations, bladder ML model 530 and/or prostate ML model 560 may be trained using ultrasound images obtained via transabdominal imaging. Additionally, or alternatively, bladder ML model 530 and/or prostate ML model 560 may be trained using a training set that includes different types of images. As an example, bladder ML model 530 and/or prostate ML model 560 may be trained using TRUS ultrasound image. As another example, bladder ML model 530 and/or prostate ML model 560 may be trained using MM images of bladders and/or prostates. The MM images may be obtained, for example, from a public MM database. The obtained MM images may include labels, such as a shape label, a size label, a medical diagnosis label, a clinically derived value label, and/or another type of label that may be used for supervised learning in training bladder ML model 530 and/or prostate ML model 560. The labels may enable extraction of image independent features that may be used by bladder ML model 530 and/or prostate ML model 560. For example, the labels may be used to obtain a statistical shape model of a particular type of bladder or prostate (e.g., based on images from a database of MRI bladder and/or prostate images) to facilitate training bladder ML model 530 and/or prostate ML model 560. Furthermore, in some implementations, bladder ML model 530 and/or prostate ML model 560 may implement any combination of machine learning with algorithmic image processing techniques. Moreover, in some implementations, bladder ML model 530 and/or prostate ML model 560 may include a "manual caliper" option to "manually" adjust the segmentation output of a machine learning model. For example, a user may be presented with a user interface to enable the user to adjust the boundary of a bladder and/or the boundary of a prostate, identified by bladder ML model 530 or prostate ML model 560, by manipulating a pointer on the display or using keypad commands to adjust the identified boundary. As another example, the user interface may enable the user to manually select a set of seed points on an image and the set of seed points may be used by bladder ML model 530 or prostate ML model 560 to perform a segmentation.

Size/volume/shape calculator 570 may calculate the size, volume, and/or shape of the patient's prostate based on an identified boundary, set of boundaries, and/or generated surface of the patient's prostate. As an example, size/volume/shape calculator 570 may calculate an area enclosed within an identified boundary in an ultrasound image to determine a cross-sectional area of the prostate in a particular plane. Additionally, or alternatively, size/volume/shape calculator 570 may determine the size of the prostate in a particular direction (e.g., the width, length, height, etc.). Furthermore, size/volume/shape calculator 570 may determine a volume of a patient's prostate based on a boundary generated using a set of ultrasound images from a 3D scan. Alternatively, size/volume/shape calculator 570 may add up a set of areas of different cross-sections, and use a distance between the different cross-sections to determine the thickness of each cross-section, to compute a volume for the patient's prostate.

Shape analyzer 575 may analyze a determined shape of the patient's prostate and/or the shape of another segmented structure, such as the patient's bladder. As an example, shape analyzer 575 may determine whether the determined shape of the patient's prostate falls within a normal/healthy range of shapes for a particular age group and/or whether the determined shape is indicative of a lesion. As another example, shape analyzer 575 may compute a IPP volume for the patient's prostate based on the determined shape of the prostate and based on the determined bladder boundary for the patient.

Recommendation manager 580 may generate a recommendation based on information received from prostate ML model 560, size/volume/shape calculator 570, and/or shape analyzer 575 based on a change in the size, shape, and/or volume of the patient's prostate from a previous visit based on a comparison of ultrasound scans, based on a detected lesion or area of concern, based on the determined size/volume/shape of the patient's prostate combined with a clinically derived value (e.g., a PSA value, etc.), and/or based on other obtained or generated information.

As an example, recommendation manager 580 may generate a recommendation for a medical intervention based on the determined size, volume, or shape of the patient's prostate, based on a PSA/volume value, and/or based on another determination. For example, recommendation manager 580 may recommend additional imaging, a biopsy, a resection, and/or another type of medical procedure. As another example, recommendation manager 580 may generate a risk prediction based on the determined size, volume, and/or shape of the patient's prostate. For example, recommendation manager 580 may generate a quantitative clinical grading value that indicates to what extent the patient's prostate will likely increase in size, cause urine retention and/or another type of symptom, or develop into a particular medical condition.

Additionally, recommendation manager 580 may generate a recommendation to improve measurement of the determined size, volume, and/or shape of the patient's prostate. The recommendation may include at least one of a recommendation to adjust a position or angle of the ultrasound probe, a recommendation to the patient to drink water or another fluid, or a recommendation to address a detected artefact or interference in an ultrasound image.

Moreover, recommendation manager 580 may use the determined size, volume, and/or shape of the patient's prostate to predict a change in the size of the patient's prostate in the future (e.g., over an upcoming number of years, etc.), to predict an outcome of a medical prostate reduction treatment, and/or to predict other aspects relating to the patient's prostate.

Although FIG. 5 shows exemplary components of controller unit 120, in other implementations, controller unit 120 may include fewer components, different components, additional components, or differently arranged components than depicted in FIG. 5. Additionally, or alternatively, one or more components of controller unit 120 may perform one or more tasks described as being performed by one or more other components of controller unit 120. As an example, in some implementations, a single ML model may be trained to perform segmentation on both the bladder and the prostate. The single ML model may calculate the size/volume/shape of the bladder and the size/volume/shape of the prostate and/or output one or more recommendations based on the calculated size/volume/shape of the bladder and/or prostate. As another example, controller unit 120 may include additional functional components for characterizing other organs or tissues. For example, controller unit 120 may include a bladder mode to scan and assess the size, volume, and/or shape of a patient's bladder, and a prostate mode to scan and assess the size, volume, and/or shape of the patient's prostate. A user may be able to toggle between the bladder mode and the prostate mode by pressing a button, activating a selection object on a touchscreen, speaking a command, and/or performing another type of action.

Figure 6:
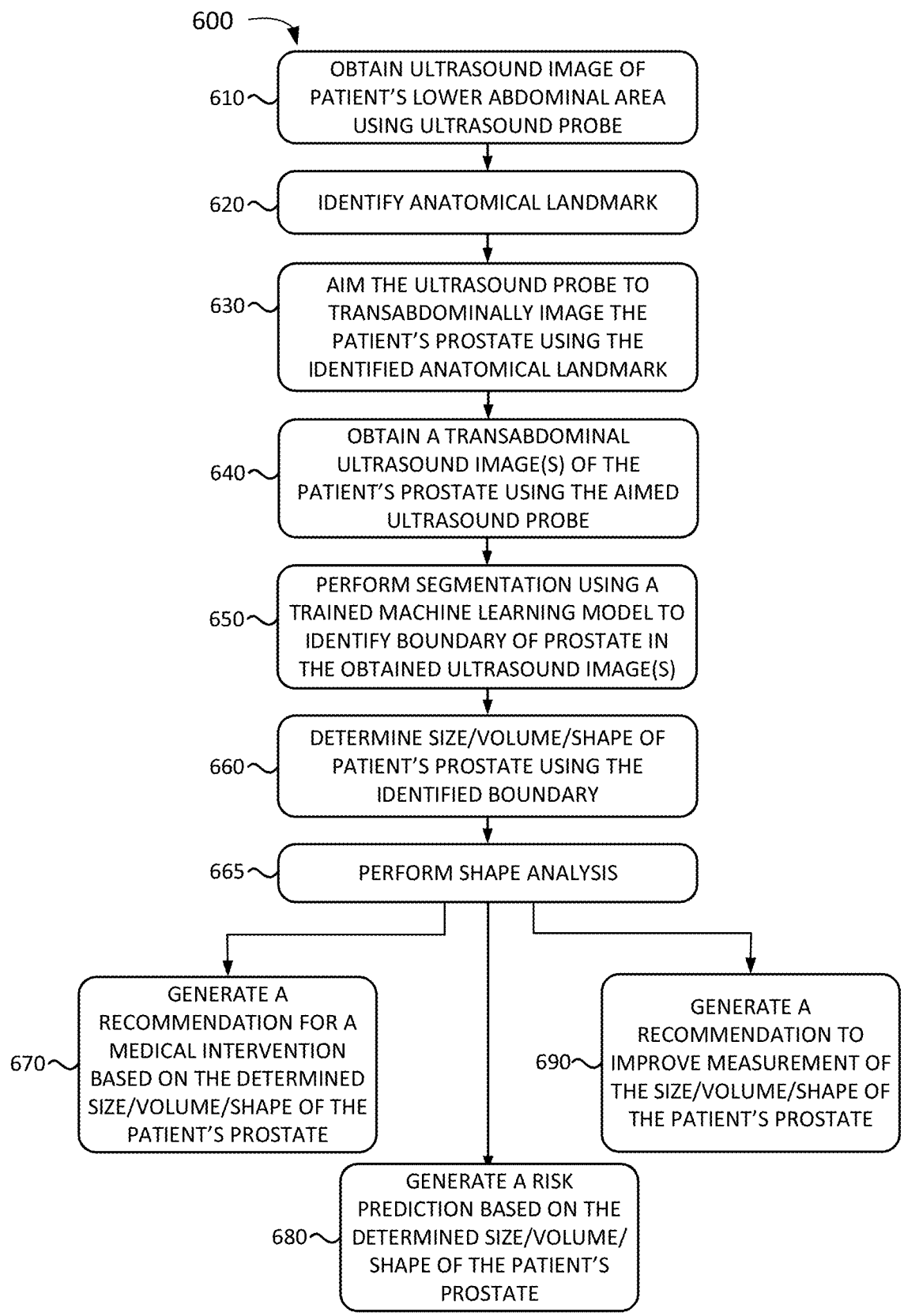
FIG. 6 is a flowchart of a process for analyzing ultrasound images of a prostate using machine learning according to an implementation described herein.

FIG. 6 is a flowchart of a process for analyzing ultrasound images of a prostate using machine learning according to an implementation described herein. In some implementations, the process of FIG. 6 may be performed by ultrasound system 100. In other implementations, some or all of the process of FIG. 6 may be performed by another device or a group of devices separate from ultrasound system 100.

The process of FIG. 6 may include obtaining an ultrasound image of a patient's lower abdominal area using an ultrasound probe (block 610), identifying an anatomical landmark in the obtained ultrasound image (block 620), and aiming the ultrasound probe to transabdominally image the patient's prostate using the identified anatomical landmark as a reference point (block 630). For example, an operator may select to initiate an ultrasound scan of a patient's prostate using controller unit 120. The user may be instructed to place ultrasound probe 110 over the patient's bladder area and to initiate a scan. Ultrasound probe 110 may capture one or more ultrasound images of the patient's bladder.

Bladder ML model 530 may perform segmentation to identify the back wall of a bladder and aiming manager 540 may determine an aiming zone for ultrasound probe 110 based on the identified anatomical landmark, such as, for example, the identified back wall of the bladder. User interface 550 may display an ultrasound image that includes the identified back wall of the bladder and the determined aiming zone. The operator may then aim ultrasound probe 110 to point into the determined aiming zone. Additionally, or alternatively, controller unit 120 may generate a set of instructions to assist the operator in aiming ultrasound probe 110 within the determined aiming zone. In other implementations, a different anatomical landmark may be used, such as a different wall of the bladder, a wall of the rectum, the pubic bone, the prostate itself, and/or another type of anatomical landmark in the prostate region of the patient's body. In some implementations, controller unit 120 may additionally automatically adjust the depth of field of ultrasound probe 110 based on the determined aiming zone.

Transabdominal ultrasound image(s) of the patient's prostate may be obtained using the aimed ultrasound probe (block 640). For example, controller unit 120 may generate an indication that ultrasound probe 110 is properly aligned to scan the patient's prostate and the operator may initiate an ultrasound scan of the patient's prostate. For example, the operator may initiate a 3D scan of the patient's prostate and ultrasound probe 110 may capture ultrasound images in a set of planes (e.g., a set of radial planes around a centerline of ultrasound probe 110, et.). The operator may select to capture B-mode ultrasound images (e.g., fundamental, harmonic and/or compounded, etc.), P-mode images, Doppler ultrasound images, M-mode images, elastography, and/or other types of ultrasound images. As an example, Color Doppler may be used to image normal and abnormal flow of fluids (e.g., blood flow) within the prostate. As another example, elastography may be used to determine tissue stiffness, as areas of different stiffness may be associated with a pathology and may be used for prostate cancer detection and characterization.

While above example describes imaging the bladder first and using an anatomical landmark associated with the bladder (e.g., the back wall of the bladder) to aim ultrasound probe 110, followed by imaging of the prostate, imaging of the bladder may not be needed to be performed first. For example, the patient's prostate and bladder area may be imaged at the same time or the patient's prostate may be imaged directly. For example, ultrasound system 100 may aim ultrasound probe 110 by identifying the prostate in a captured ultrasound image, aim ultrasound probe 110 to direct more ultrasound energy directly to the identified prostate, followed by a more detailed scan (e.g., a 3D scan) of the identified prostate using the aimed ultrasound probe 110. Furthermore, in some implementations, ultrasound probe 100 may have a large field of view that does not require aiming and the patient's prostate may be scanned without aiming ultrasound probe 110.

Segmentation may be performed using a trained machine learning model to identify a boundary of the prostate in the obtained ultrasound image(s) (block 650). For example, prostate ML model 560, and/or another trained ML model, may perform segmentation to identify the boundaries of the prostate in a set of 2D ultrasound images. Prostate ML model 560 may then stitch together or otherwise combine the boundaries from the individual ultrasound images to generate a 3D surface of the prostate. In some implementations, prostate ML model 560 may classify a segmented prostate into a particular size category (e.g., small, normal, enlarged, etc.). Additionally, prostate ML model 560 may compare an identified boundary of the patient's prostate with previously determined boundary of the patient's prostate during a previous visit (e.g., by retrieving ultrasound images associated with the patient's records). Moreover, in some implementations, prostate ML model 560, or another ML model, may determine whether the patient's prostate includes a lesion or an area of concern based on, for example, identifying a boundary of an area within the prostate that reflected ultrasound signals differently from other areas of the prostate by at least a threshold amount. Furthermore, controller unit 120 may provide a user interface to enable a user to manually adjust the identified boundary of the prostate or to define a set of points for performing the segmentation process.

The size, volume, and/or shape of the patient's prostate may be determined using the identified boundary (block 660) and shape analysis may be performed (bock 665). For example, controller unit 120 may calculate an area enclosed within the identified boundary in an ultrasound image to determine a cross-sectional area of the prostate in a particular plane and may add up a set of areas of different cross-sections, and use a distance between the different cross-sections to determine the thickness of each cross-section, to compute a volume for the patient's prostate. Alternatively, controller unit 120 may calculate a volume within a 3D prostate boundary generated based on a collection of ultrasound images obtained during a 3D scan. Controller unit 120 may also determine the size and/or shape of the prostate in a particular direction (e.g., the width, length, height, etc.) and/or may determine if the shape of the prostate falls outside a range or normal shapes or is associated with a particular pathology. Furthermore, controller unit 120 may generate one or more clinical values based on the determined size, volume, and/or shape of the patient's prostate, such as a PSA/volume value, an IPP value, and/or another type of clinical value. As an example, controller unit 120 may calculate an IPP value based on the determined size, volume, or shape of the patient's prostate. As another example, controller unit 120 may calculate a PSA to volume ratio based on the determined size, volume, or shape of the patient's prostate combined with a clinically derived PSA level for the patient (e.g., determined via a blood test, etc.).

A recommendation for a medical intervention may be generated based on the determined size, volume, and/or shape of the patient's prostate (block 670). For example, controller unit 120 may determine whether the size, volume, and/or shape of the patient's prostate is within a particular range for the patient's age group and/or may determine a value based on the determined size/volume/shape of the prostate combined with a clinically derived value (e.g., a PSA/volume value, etc.). Furthermore, controller unit 120 may compare the determined size, volume, and/or shape of the patient's prostate to a size, volume, and/or shape determined during a previous visit to calculate a change in the size, volume, and/or shape over time. Additionally, controller unit 120 may determine whether any lesions or areas of concern have been detected. For example, an elastography scan may identify an area of higher stiffness which may indicate a tumor. Thus, controller unit 120 may generate a recommendation for additional imaging, a biopsy, a resection, and/or another type of medical procedure.

A risk prediction may be generated based on the determined size, volume, and/or shape of the patient's prostate (block 680). For example, controller unit 120 may generate a quantitative clinical grading value that indicates to what extent the patient's prostate will likely increase in size, cause urine retention and/or another type of symptom, or develop into a particular medical condition. Additionally, controller unit 120 may use the determined size, volume, and/or shape of the patient's prostate to predict a change in the size of the patient's prostate in the future (e.g., over an upcoming number of years, etc.), to predict an outcome of a medical prostate reduction treatment, and/or to predict other aspects relating to the patient's prostate.

A recommendation to improve measurement of the size, volume, and/or shape of the patient's prostate may be generated (block 690). As an example, controller unit 120 may determine that the calculated size, volume, and/or shape of the patient's prostate is outside an expected range and may determine that ultrasound probe 110 was not positioned correctly. In response, controller unit 120 may generate a recommendation, presented via display 122, to adjust a position or angle of the ultrasound probe. As another example, controller unit 120 may determine that the ultrasound signals are not travelling through the bladder and are experience too much reflection in the bladder. For example, controller unit 120 may determine that the patient's bladder is too empty based on a determined size of the bladder. In response, controller unit 120 may generate a recommendation for the patient to drink water or another fluid to increase the fluid in the bladder, which may result in better imaging of the prostate. As yet another example, controller unit 120 may detect an artefact or interference in an ultrasound image. For example, prostate ML model 560 may be trained to detect colon gas. Alternatively, controller unit 120 may assume colon gas is present if the size of the patient's prostate is determined to be outside an expected range due to the colon being misinterpreted as part of the prostate. In response, controller unit 120 may generate a recommendation to the patient to remove bowel gas.

Figure 7:
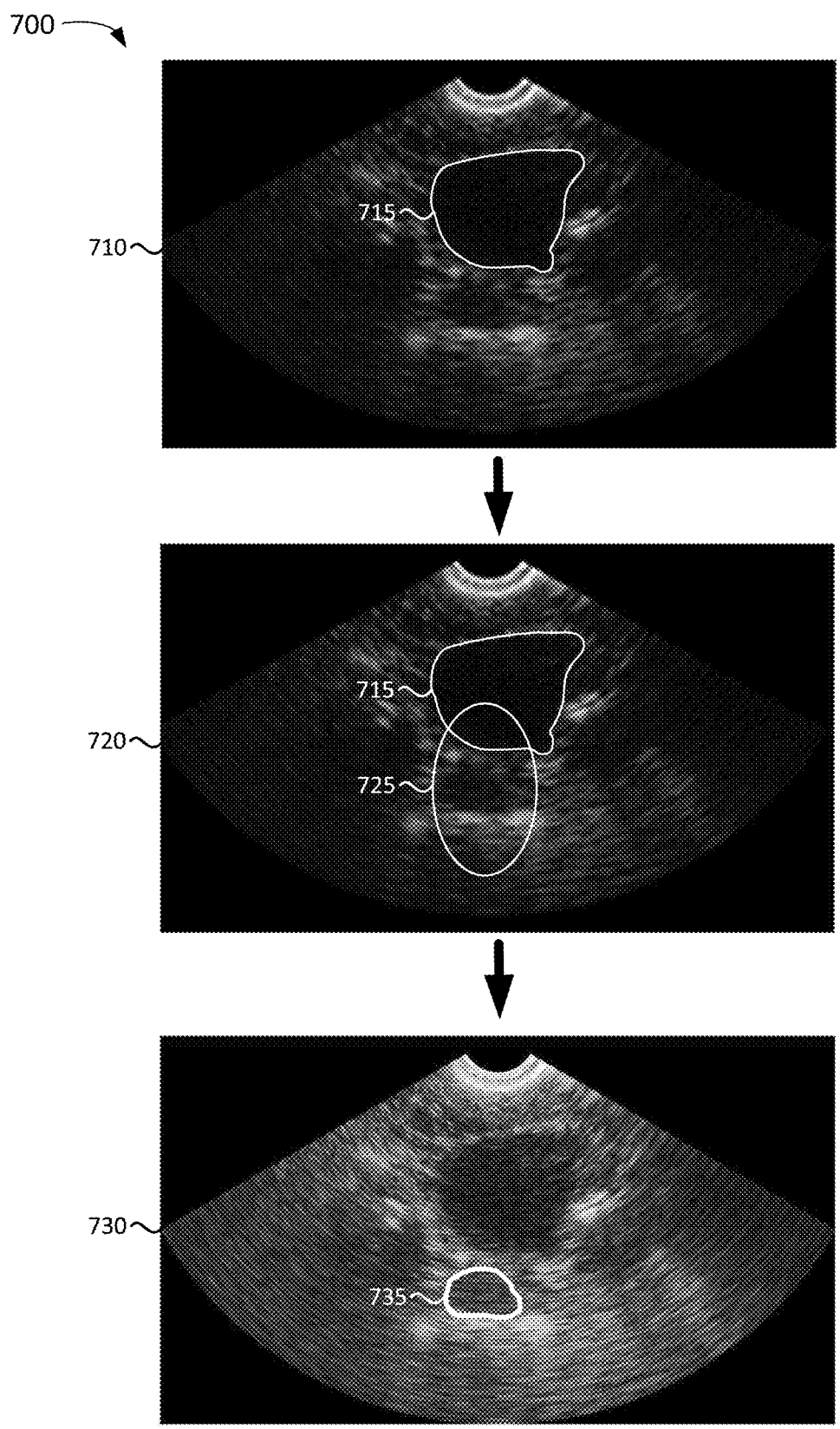
FIG. 7 is a diagram illustrating segmentation of a bladder, identification of an aiming zone, and segmentation of a prostate according to an implementation described herein.

FIG. 7 is a diagram illustrating segmentation of a bladder, identification of an aiming zone, and segmentation of a prostate according to an implementation described herein. Ultrasound image 710, which may be presented on display 122, may include an identified boundary 715 of the patient's bladder as determined through segmentation by bladder ML model 530. Ultrasound image 720, presented subsequently, may include an identified aiming zone 725 for ultrasound probe 110. Aiming zone 725 may be determined based on the back wall of identified boundary 715 and/or another identified anatomical landmark, such as a side wall of the bladder, a pubic bone shadow, the prostate itself, and/or another type of anatomical landmark. Controller unit 120 may then optimize the settings of ultrasound probe 110 (e.g., by adjusting the depth of field) to capture ultrasound images in aiming zone 725. Furthermore, the operator may be instructed to move/tilt ultrasound probe 110 to optimize image capture in aiming zone 725. Ultrasound image 730 may be presented on display 122 after the patient's prostate has been imaged using aiming zone 725 and segmentation has been performed by prostate ML model 560 to identify boundary 735 of the patient's prostate.

Figure 8:
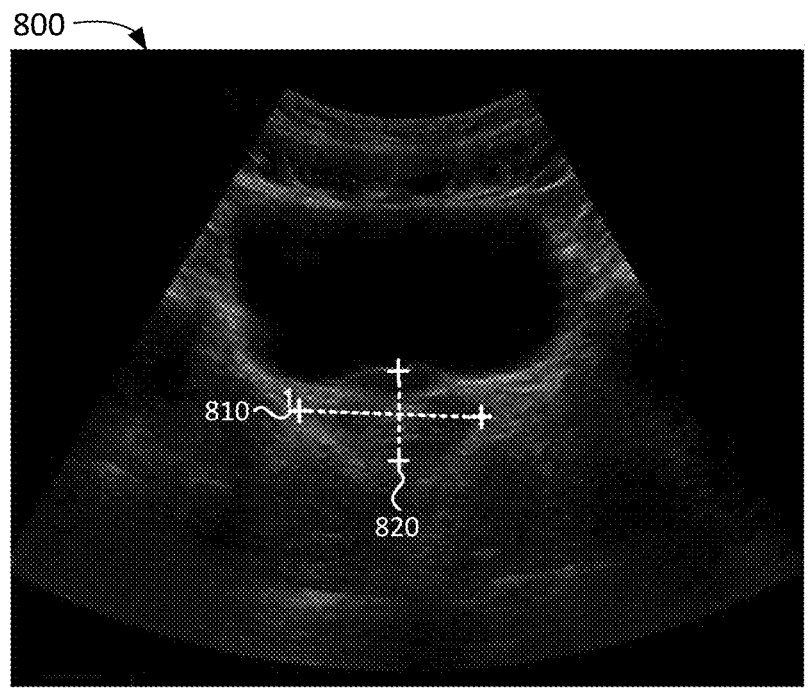
FIG. 8 is a diagram illustrating determination of the size of a prostate according to an implementation described herein.

FIG. 8 is a diagram 800 illustrating determination of the size of a prostate according to an implementation described herein. As shown in FIG. 8, diagram 800 includes an ultrasound image of a patient's prostate in which the size of the prostate has been determined in two different dimensions based on segmentation performed by prostate ML model 560. For example, prostate ML model 560 may determine a width 810 of the prostate and a height 820 of the prostate in a particular plane in which the ultrasound image has been captured.

Figure 9:
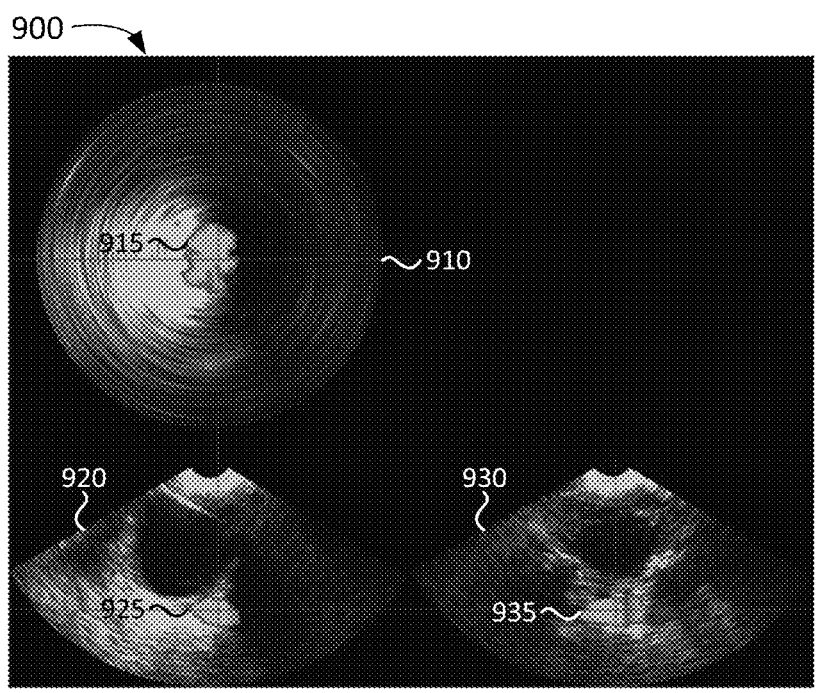
FIG. 9 is a diagram illustrating determination of the size of a prostate from a three-dimensional (3D) ultrasound scan according to an implementation described herein.

FIG. 9 is a diagram 900 illustrating determination of the volume of a prostate from 3D ultrasound scan according to an implementation described herein. As shown in FIG. 9, diagram 900 illustrates a generated 3D boundary surface of a patient's prostate based on a set of ultrasound images obtained during a 3D scan. A first ultrasound image 910 includes a boundary 915 of the prostate in a coronal plane, a second ultrasound image 920 includes a boundary 925 of the prostate in a sagittal plane, and a third ultrasound image 930 includes a boundary 935 of the prostate in a transverse plane.

Figure 10:
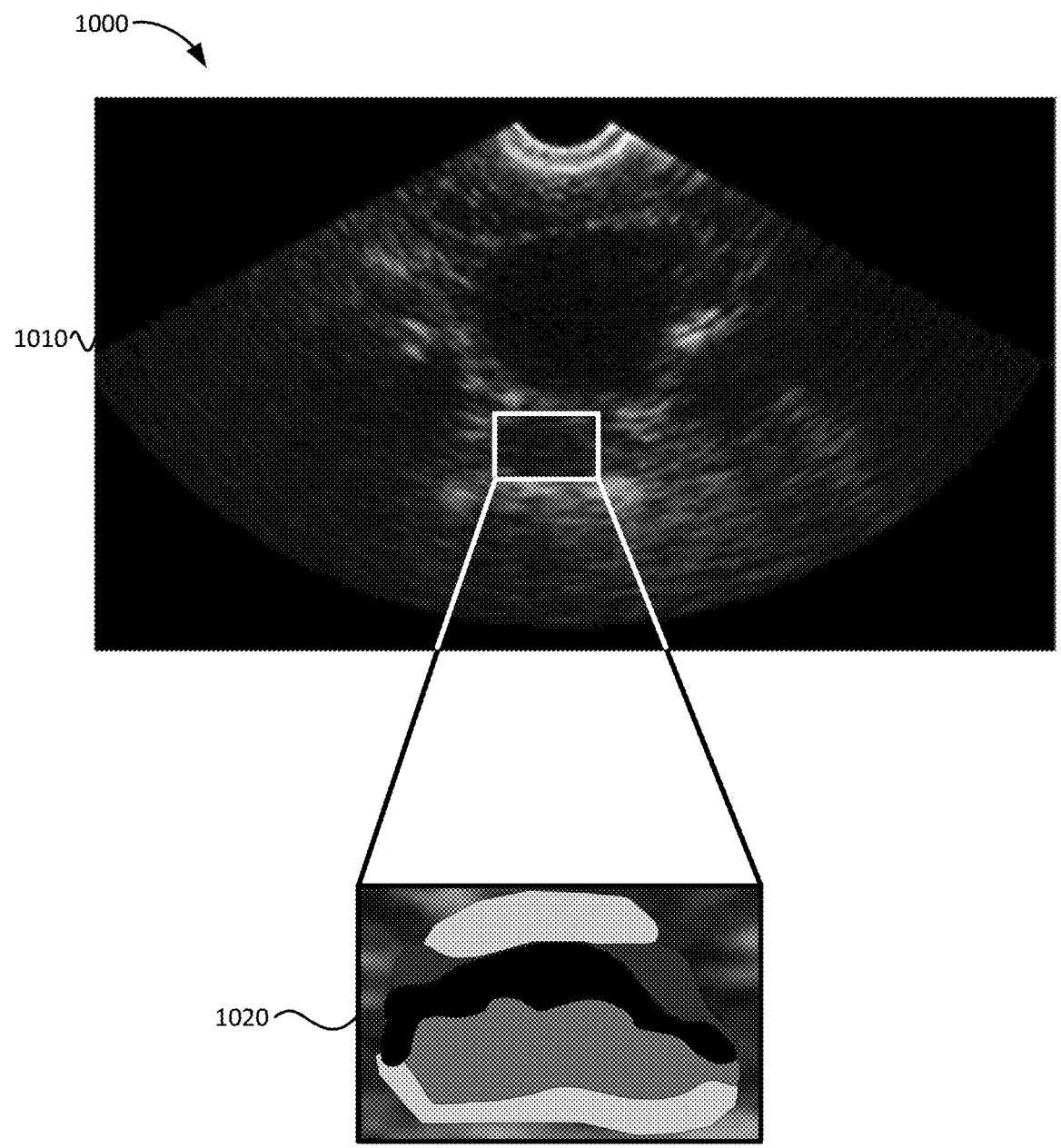
FIG. 10 is a diagram illustrating the use of elastography for prostate characterization according to an implementation described herein.

FIG. 10 is a diagram 1000 illustrating the use of elastography for prostate characterization according to an implementation described herein. As shown in FIG. 10, diagram 1000 illustrates an ultrasound image 1010 that has been correlated with an elastography image 1020 processed using segmentation to identify areas with different values of tissue stiffness, with different colors and/or shading values representing different tissue stiffness values. Thus, prostate ML model 560 may be trained to perform segmentation on elastography images to identify areas associated with a particular tissue stiffness and/or to identify a particular pathology associated with a particular tissue stiffness. Furthermore, prostate ML model 560 may be trained to perform histological, morphological, and/or sonographic characterization of a prostate based on B-mode brightness, elastography images, and/or Doppler ultrasound images. As an example, prostate ML model 560 may be trained to identify calcium deposits, adenomas, and/or other types of abnormalities. As another example, prostate ML model 560 may be trained to identify an outer peripheral zone and/or inner transition zone of the prostate.

Figure 11:
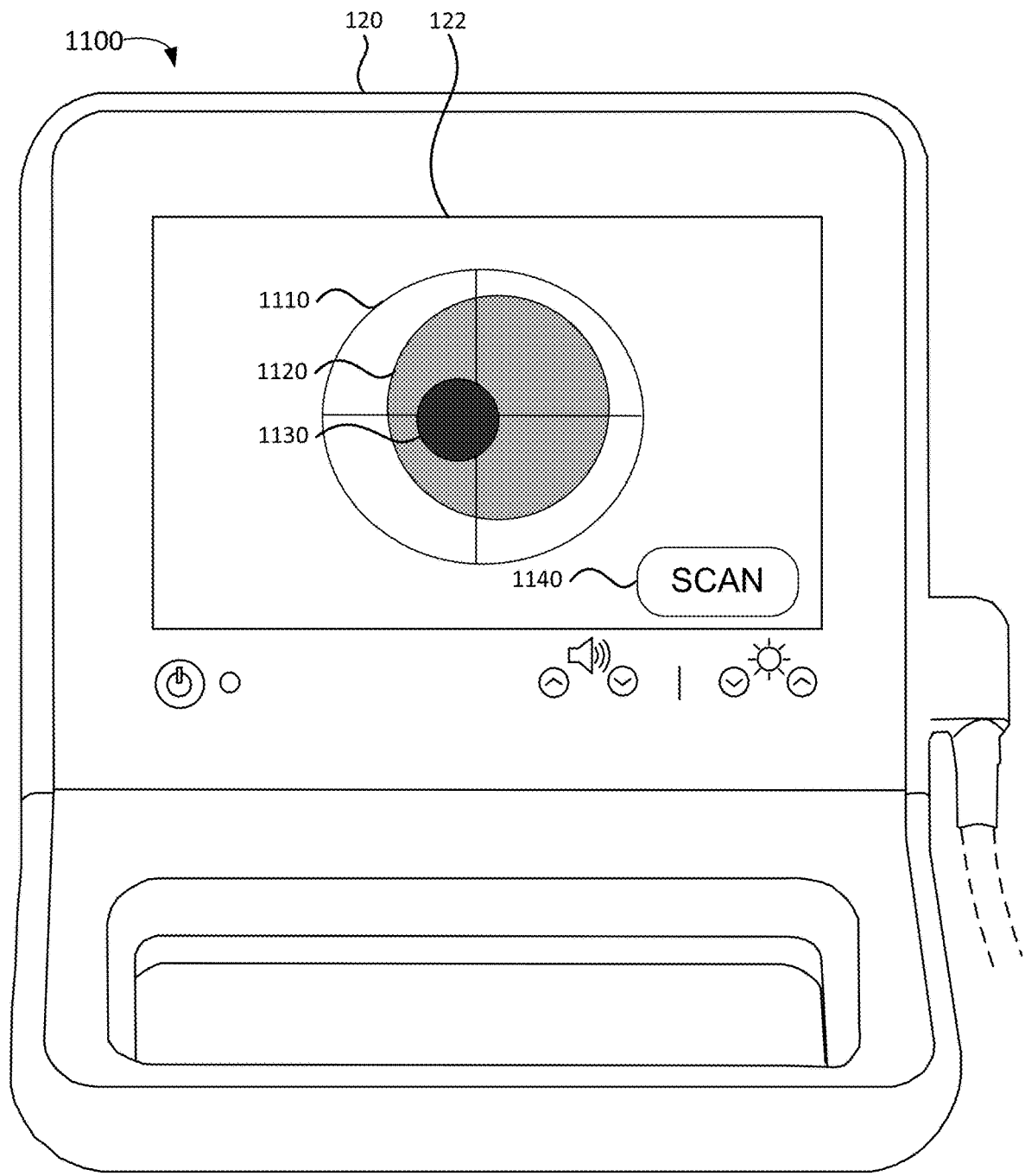
FIG. 11 is a diagram illustrating a first exemplary user interface according to an implementation described herein.

FIG. 11 is a diagram illustrating a first exemplary user interface 1100 according to an implementation described herein. As shown in FIG. 11, user interface 1100 may be presented on display 122 of controller unit 120 during aiming of ultrasound probe 110. User interface 110 may present a real-time graphical representation of detected body organs/structures to aid an operator in centering ultrasound probe 110 for a more accurate measurement. Such a graphical representation of obtained ultrasound data may be used to center ultrasound probe 110. In such a display mode, display 122 may include a reticle 1110 representing the current aiming direction of ultrasound probe 110, bladder projection 1120 representing the size and position of the determined largest cross-section of the patient's bladder, and prostate projection 1130 representing the determined the size and position of the determined largest cross-section of the patient's prostate. As the operator moves ultrasound probe 110 around, the positions of reticle 1110, bladder projection 1120, and prostate projection 1130 may be updated. When the operator is satisfied with the alignment and position of ultrasound probe 110, the operator may activate scan button 1140 to perform an ultrasound scan.

Figure 12:
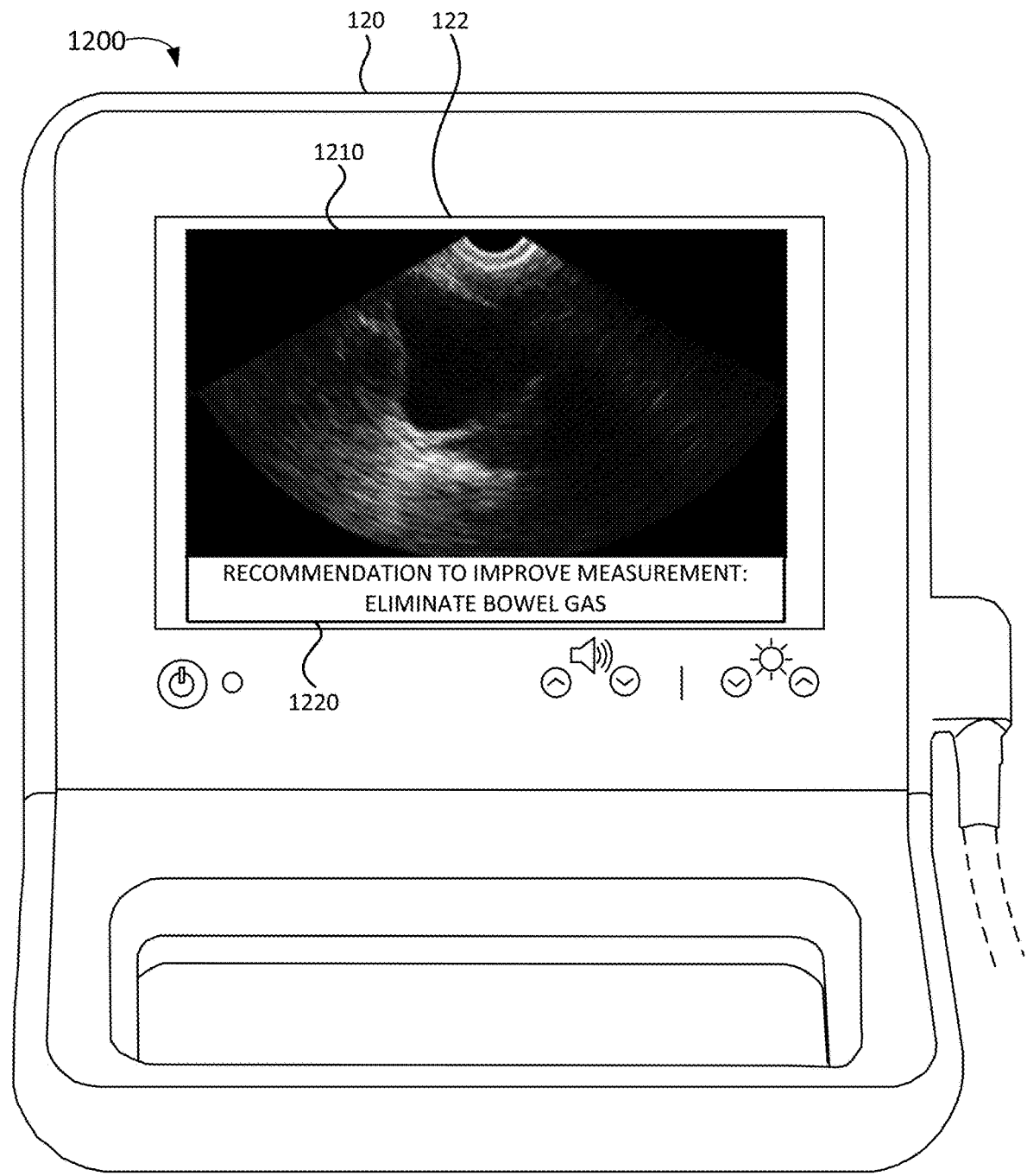
FIG. 12 is a diagram illustrating a second exemplary user interface according to an implementation described herein.

FIG. 12 is a diagram illustrating a second exemplary user interface 1200 according to an implementation described herein. As shown in FIG. 12, user interface 1200 may be presented on display 122 of controller unit 120 and may include a captured ultrasound image 1210. Ultrasound image 1210 may include a prostate that is obscured due to gas in the colon. Controller unit 120 may detect the presence of colon gas as a result of poor segmentation of the prostate (e.g., an inability to identify the boundary of the prostate), as a result of detecting a boundary classified as a colon boundary, and/or using another technique. In response, controller unit 120 may generate a recommendation 1220 to have the patient eliminate bowel gas.

Figure 13:
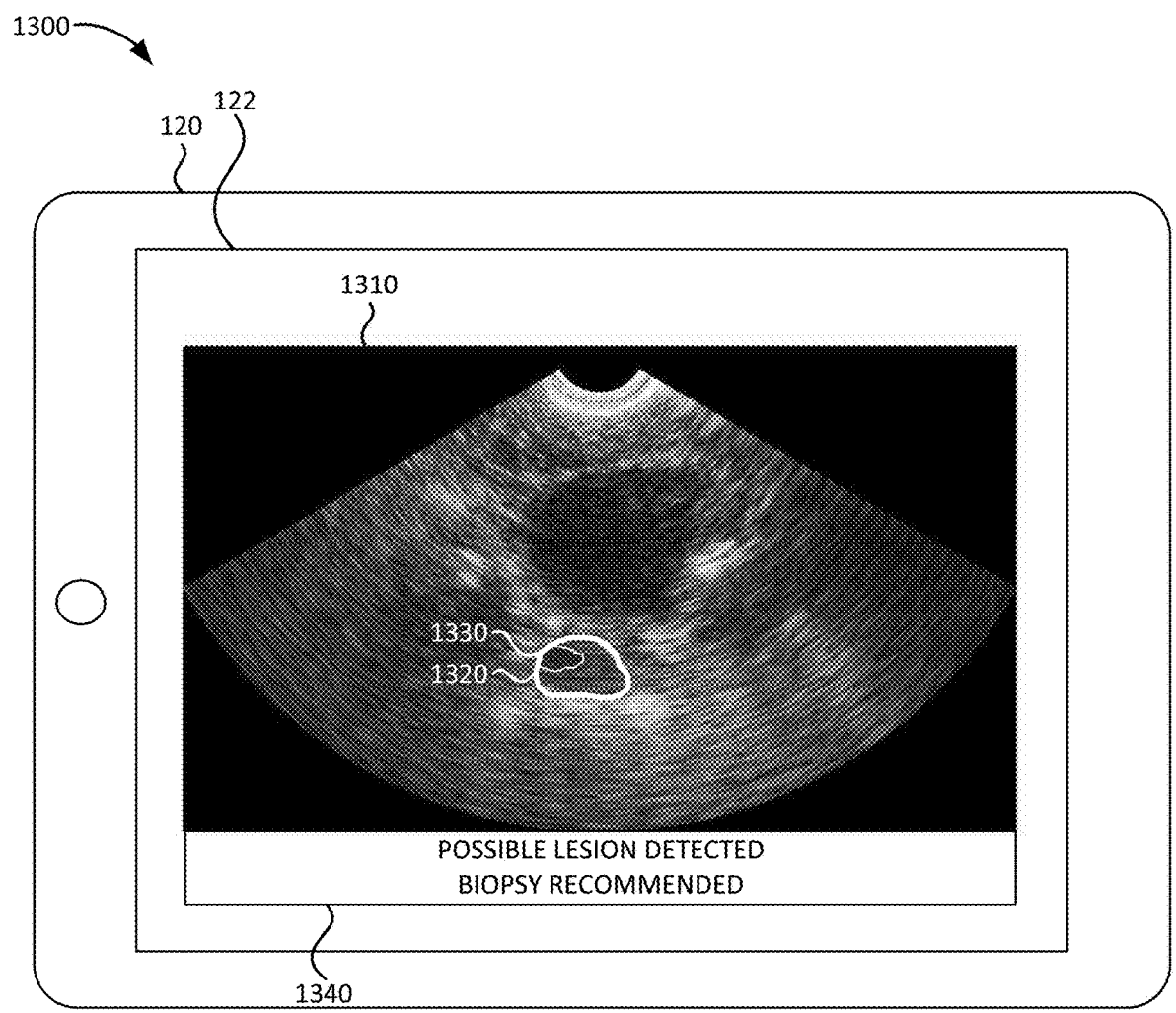
FIG. 13 is a diagram illustrating a third exemplary user interface according to an implementation described herein.

FIG. 13 is a diagram illustrating a third exemplary user interface 1300 according to an implementation described herein. As shown in FIG. 13, user interface 1300 may be presented on display 122 of controller unit 120 and may include a captured ultrasound image 1310. In the example of FIG. 13, controller unit 120 may correspond to a tablet computer device communicating with ultrasound probe 110 using a wireless connection. Ultrasound image 1310 may include an identified prostate boundary 1320. Additionally, ultrasound image 1320 may include an identified lesion boundary 1330. In response, controller unit 120 may generate a recommendation 1340 to perform a biopsy on the lesion.

Figure 14:
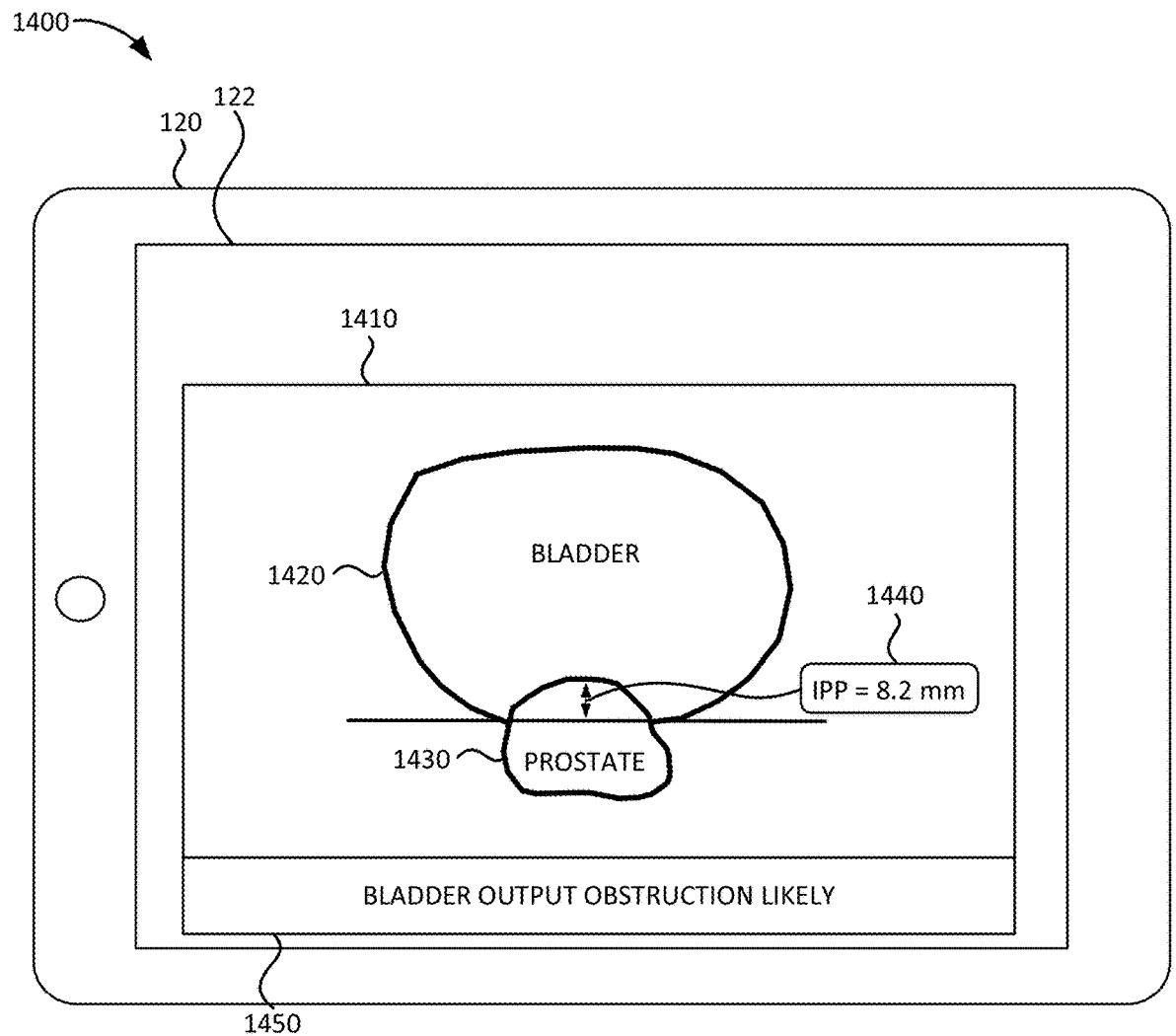
FIG. 14 is a diagram illustrating a fourth exemplary user interface according to an implementation described herein.

FIG. 14 is a diagram illustrating a fourth exemplary user interface 1400 according to an implementation described herein. As shown in FIG. 14, user interface 1400 may be presented in display 122 of controller unit 120 and may include a recommendation generated based on a determined clinical value. In the example of FIG. 14, controller unit 120 may correspond to a tablet computer device communicating with ultrasound probe 110 using a wireless connection. User interface 1400 may include a graphical representation 1410 of a computed IPP value. Graphical representation 1410 may include a determined bladder boundary 1420, a determined prostate boundary 1430, and a computed IPP value 1440 based on the determined bladder boundary 1420 and prostate boundary 1430. User interface 1400 may further include an analysis 1450 based on the computed IPP value 1440. For example, analysis 1450 may indicate that a bladder output obstruction (BOO) is likely based on the computed IPP value 1440.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

For example, while a series of blocks have been described with respect to FIG. 6, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/ "comprising" when used in this specification are taken to specify the presence of stated features, integers, steps or components but does not preclude the presence or addition of one or more other features, integers, steps, components or groups thereof.

The term "logic," as used herein, may refer to a combination of one or more processors configured to execute instructions stored in one or more memory devices, may refer to hardwired circuitry, and/or may refer to a combination thereof. Furthermore, a logic may be included in a single device or may be distributed across multiple, and possibly remote, devices.

For the purposes of describing and defining the present invention, it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

No element, act, or instruction used in the present application should be construed as critical or essential to the embodiments unless explicitly described as such. Also, as used herein, the article "a" is intended to include one or more items. Further, the phrase "based on" is intended to mean "based, at least in part, on" unless explicitly stated otherwise.

What is claimed is:

1. A method performed by a computing device, the method comprising:
    obtaining, by the computing device, an ultrasound image of a patient's bladder area by controlling an ultrasound transducer in an ultrasound probe;
    identifying, by the computing device, an anatomical landmark in the ultrasound image;
    determining, by the computing device, an aiming zone to image the patient's prostate based on the identified anatomical landmark;
    aiming, by the computing device, the ultrasound probe to transabdominally image the patient's prostate based on the determined aiming zone, wherein the aiming includes adjusting a depth of field of the ultrasound probe;
    obtaining, by the computing device, a transabdominal image of the patient's prostate using the aimed ultrasound probe, wherein obtaining the transabdominal image includes driving the ultrasound transducer in the ultrasound probe;
    performing, by the computing device, a segmentation process on the obtained transabdominal image of the patient's prostate using a machine learning model to identify a boundary of the prostate in the transabdominal image of the patient's prostate;
    determining, by the computing device, a size, volume, or shape of the patient's prostate using the identified boundary of the prostate; and
    generating, by the computing device, a recommendation to improve measurement of the determined size, volume, or shape of the patient's prostate based on the determined size, volume, or shape of the patient's prostate, wherein generating the recommendation includes at least one of:
        generating a recommendation to adjust a position or angle of the ultrasound probe based on determining that the determined size, volume, or shape of the patient's prostate is outside an expected range;
        generating a recommendation to the patient to drink water or fluid; or
        generating a recommendation to address a detected artifact or interference in the obtained transabdominal image.

2. The method of claim 1, wherein identifying the anatomical landmark in the ultrasound image includes:
    identifying a wall of a bladder as the anatomical landmark in the obtained ultrasound image; and
    wherein the aiming the ultrasound probe to transabdominally image the patient's prostate based on the determined aiming zone is performed using the identified wall of the bladder as a reference.

3. The method of claim 1, further comprising:
    generating a medical recommendation based on the determined size, volume, or shape of the patient's prostate.

4. The method of claim 1, further comprising:
    generating a risk prediction based on the determined size, volume, or shape of the patient's prostate.

5. The method of claim 1, further comprising:
    calculating an intravesical prostate protrusion (IPP) value using the identified boundary of the patient's prostate.

6. The method of claim 1, wherein determining a size, volume, or shape of the patient's prostate using the identified boundary of the prostate includes:
    determining the volume of the patient's prostate; the method further comprising:
    calculating a prostate specific antigen (PSA) to volume ratio based on the determined volume of the patient's prostate.

7. The method of claim 1, wherein the ultrasound transducer includes a dual focus ultrasound transducer, and wherein obtaining the transabdominal image of the patient's prostate using the aimed ultrasound probe includes:
    driving the dual focus ultrasound transducer in the ultrasound probe, wherein an outer element of the dual focus ultrasound transducer includes a first ultrasound transducer driven at a first frequency or frequency range, and wherein an inner element of the dual focus ultrasound transducer includes the second ultrasound transducer driven at a second frequency or frequency range.

8. The method of claim 1, wherein obtaining the transabdominal image of the patient's prostate using the aimed ultrasound probe includes:
    obtaining a set of three-dimensional (3D) ultrasound scan images of the patient's prostate.

9. The method of claim 1, wherein obtaining the transabdominal image of the patient's prostate using the aimed ultrasound probe further includes:
obtaining an elastography ultrasound image, the method further comprising:
identifying an area associated with a particular tissue stiffness based on the obtained elastography ultrasound image.

10. The method of claim 1, wherein aiming the ultrasound probe to transabdominally image the patient's prostate based on the determined aiming zone includes:
obtaining information from at least one of a position sensor or a pressure sensor located in the ultrasound probe.

11. The method of claim 1, further comprising:
providing a user interface to enable a user to manually adjust the identified boundary of the prostate or to define a set of points for performing the segmentation process.

12. The method of claim 1, wherein the transabdominal image of the patient's prostate includes at least one of a B-mode ultrasound image, a Doppler mode ultrasound image, or an elastography ultrasound image.

13. The method of claim 1, wherein generating the recommendation includes:
determining that the determined size, volume, or shape of the patient's prostate is outside the expected range; and
generating the recommendation to adjust a position or angle of the ultrasound probe based on determining that the determined size, volume, or shape of the patient's prostate is outside the expected range.

14. The method of claim 1, wherein generating the recommendation includes:
determining that the patient's bladder includes insufficient fluid; and
generating the recommendation to the patient to drink water or fluid, in response to determining that the patient's bladder includes insufficient fluid.

15. The method of claim 1, wherein generating the recommendation includes:
determining that the patient's bladder area includes the detected artifact or interference; and
generating a recommendation to address the detected artefact or interference in the obtained transabdominal image.

16. The method of claim 2, wherein identifying the wall of the bladder as the anatomical landmark in the obtained ultrasound image includes:
performing another segmentation process on the obtained ultrasound image using another trained machine learning model to identify the wall of the bladder.

17. A system comprising:
an ultrasound probe; and
a controller unit configured to:
obtain an ultrasound image of a patient's bladder area by controlling at least one ultrasound transducer in the ultrasound probe;
identify an anatomical landmark in the ultrasound image;
determine an aiming zone to image the patient's prostate based on the identified anatomical landmark;
aim the ultrasound probe to transabdominally image the patient's prostate based on the determined aiming zone;
obtain a transabdominal image of the patient's prostate using the aimed ultrasound probe, wherein obtaining the transabdominal image includes driving first and second ultrasound transducers in the ultrasound probe;
perform a segmentation process on the obtained transabdominal image of the patient's prostate to identify a boundary of the prostate in the transabdominal image of the patient's prostate;
determine a size, volume, or shape of the patient's prostate using the identified boundary of the prostate; and
generate a recommendation to improve measurement of the determined size, volume, or shape of the patient's prostate based on the determined size, volume, or shape of the patient's prostate, wherein, when generating the recommendation, the controller unit is configured to at least one of:
generate a recommendation to adjust a position or angle of the ultrasound probe based on determining that the determined size, volume, or shape of the patient's prostate is outside an expected range;
generate a recommendation to the patient to drink water or fluid; or
generate a recommendation to address a detected artifact or interference in the obtained transabdominal image.

18. The system of claim 17, wherein, when identifying the anatomical landmark in the ultrasound image, the controller unit is further configured to:
identify a wall of a bladder as the anatomical landmark in the obtained ultrasound image; and
wherein, when aiming the ultrasound probe to transabdominally image the patient's prostate based on the determined aiming zone, the controller unit is configured to perform the aiming using the identified wall of the bladder as a reference.

19. The system of claim 17, wherein the controller unit is further configured to at least one of:
generate a medical recommendation for a medical intervention based on the determined size, volume, or shape of the patient's prostate; or
generate a risk prediction based on the determined size, volume, or shape of the patient's prostate.

20. The system of claim 17, wherein the at least one ultrasound transducer includes a dual focus ultrasound transducer that includes the first ultrasound transducer and the second ultrasound transducer, and wherein, when obtaining the transabdominal image of the patient's prostate using the aimed ultrasound probe, the controller unit is further configured to:
drive the dual focus ultrasound transducer in the ultrasound probe, wherein the first ultrasound transducer of the dual focus ultrasound transducer is driven at the first frequency or frequency range, and wherein the second ultrasound transducer of the dual focus ultrasound transducer is driven at the second frequency or frequency range.

21. The system of claim 17, wherein the ultrasound probe includes at least one of a position sensor or a pressure sensor, and wherein the controller unit is further configured to:
obtain information from the at least one of a position sensor or a pressure sensor located in the ultrasound probe.

22. The system of claim 17, wherein, when obtaining the transabdominal image of the patient's prostate using the aimed ultrasound probe, the controller unit is further configured to at least two of:

obtain a set of three-dimensional (3D) ultrasound scan images of the patient's prostate;
obtain a Doppler ultrasound image of the patient's prostate; or
obtain an elastography ultrasound image of the patient's prostate.

23. A device comprising:
a processor configured to:
   obtain an ultrasound image of a patient's bladder area by controlling at least one ultrasound transducer in an ultrasound probe;
   identify a wall of a bladder in the obtained ultrasound image;
   determine an aiming zone to image the patient's prostate based on the identified wall of the bladder;
   aim the ultrasound probe to transabdominally image the patient's prostate based on the determined aiming zone;
   obtain a transabdominal image of the patient's prostate using the aimed ultrasound probe, wherein obtaining the transabdominal image includes driving first and second ultrasound transducers in the ultrasound probe;
   perform a segmentation process on the obtained transabdominal image of the patient's prostate using a trained machine learning model to identify a boundary of the prostate in the transabdominal image of the patient's prostate;
   determine a size, volume, or shape of the patient's prostate using the identified boundary of the prostate; and
   generate a recommendation to improve measurement of the determined size, volume, or shape of the patient's prostate based on the determined size, volume, or shape of the patient's prostate, wherein, when generating the recommendation, the processor is configured to at least one of:
      generate a recommendation to adjust a position or angle of the ultrasound probe based on determining that the determined size, volume, or shape of the patient's prostate is outside an expected range;
      generate a recommendation to the patient to drink water or fluid; or
      generate a recommendation to address a detected artifact or interference in the obtained transabdominal image.

\* \* \* \* \*